(12) United States Patent
Ogasawara

(10) Patent No.: US 11,419,482 B2
(45) Date of Patent: Aug. 23, 2022

(54) ENDOSCOPE APPARATUS, CONTROL METHOD OF ENDOSCOPE APPARATUS, AND RECORDING MEDIUM

(71) Applicant: OLYMPUS CORPORATION, Tokyo (JP)

(72) Inventor: Masamitsu Ogasawara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 418 days.

(21) Appl. No.: 16/267,483

(22) Filed: Feb. 5, 2019

(65) Prior Publication Data

US 2019/0239725 A1 Aug. 8, 2019

(30) Foreign Application Priority Data

Feb. 7, 2018 (JP) .............................. JP2018-020411

(51) Int. Cl.
*A61B 1/00* (2006.01)
*A61B 1/045* (2006.01)
(Continued)

(52) U.S. Cl.
CPC ...... *A61B 1/00096* (2013.01); *A61B 1/00163* (2013.01); *A61B 1/00188* (2013.01);
(Continued)

(58) Field of Classification Search
None
See application file for complete search history.

(56) References Cited

U.S. PATENT DOCUMENTS 8,717,571 B2 * 5/2014 Takaoka ................ A61B 1/042
356/445
2002/0154912 A1 * 10/2002 Koseki ............. H04N 5/232945
396/429
(Continued)

FOREIGN PATENT DOCUMENTS

JP      2005-303694 A    10/2005
JP      2010-128354 A     6/2010
(Continued)

OTHER PUBLICATIONS

Japanese Office Action dated Jun. 2, 2021.

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

An endoscope apparatus includes: an insertion portion having a distal end portion; an optical path switching unit configured to switch an optical path so that only one of a first subject image and a second subject image is imaged on an image forming area, the second subject image being an image of a subject formed by light emitted from a second objective optical system disposed at the distal end portion and having an optical magnification higher than that of the first objective optical system; an imaging element configured to generate an image acquired by picking up the first subject image and the second subject image formed in the image forming area; and an endoscope processing unit configured to control switching of the optical path based on an input zoom magnification and apply image processing to the image generated by the imaging element.

19 Claims, 6 Drawing Sheets

(51) Int. Cl.
*G02B 23/24* (2006.01)
*A61B 1/05* (2006.01)

(52) U.S. Cl.
CPC .............. *A61B 1/045* (2013.01); *A61B 1/05* (2013.01); *G02B 23/2407* (2013.01); *A61B 1/00009* (2013.01); *A61B 1/00117* (2013.01)

(56) References Cited

U.S. PATENT DOCUMENTS

| | | | | |
|---|---|---|---|---|
| 2002/0161284 | A1* | 10/2002 | Tanaka | A61B 1/00101 600/176 |
| 2009/0167899 | A1* | 7/2009 | Tsuda | H04N 5/232 348/240.2 |
| 2010/0165080 | A1* | 7/2010 | Yamaguchi | A61B 1/00183 348/45 |
| 2010/0208046 | A1* | 8/2010 | Takahashi | A61B 1/042 348/65 |
| 2013/0041226 | A1* | 2/2013 | McDowall | A61B 1/00193 600/166 |
| 2013/0184530 | A1* | 7/2013 | On | A61B 1/00188 600/168 |
| 2013/0286172 | A1* | 10/2013 | Sasaki | A61B 1/000094 348/65 |
| 2014/0111628 | A1* | 4/2014 | Yoshino | G02B 7/102 348/65 |
| 2014/0204187 | A1* | 7/2014 | Sasaki | G06T 7/33 348/65 |
| 2014/0228644 | A1* | 8/2014 | Ikenaga | A61B 1/00193 600/166 |
| 2014/0300799 | A1* | 10/2014 | Yoshino | H04N 5/23212 348/347 |
| 2014/0307072 | A1* | 10/2014 | Takahashi | H04N 5/23296 348/65 |
| 2016/0119521 | A1* | 4/2016 | Zen | A61B 1/00133 348/76 |
| 2016/0295085 | A1* | 10/2016 | Aoyama | A61B 1/00188 |

FOREIGN PATENT DOCUMENTS

| | | |
|---|---|---|
| JP | 2014-028008 A | 2/2014 |
| JP | 2014-207645 A | 10/2014 |
| JP | 2014-228851 A | 12/2014 |
| JP | 2015-176009 A | 10/2015 |
| JP | 2016-218242 A | 12/2016 |
| WO | 2015/001852 A1 | 1/2015 |
| WO | 2015/056701 A1 | 4/2015 |
| WO | 2017/221507 A1 | 12/2017 |

\* cited by examiner

ENDOSCOPE APPARATUS, CONTROL METHOD OF ENDOSCOPE APPARATUS, AND RECORDING MEDIUM

BACKGROUND

Technical Field

The present invention relates to an endoscope apparatus, a control method of an endoscope apparatus, and a recording medium.

Priority is claimed on Japanese Patent Application No. 2018-020411, filed Feb. 7, 2018, the content of which is incorporated herein by reference.

Background Art

Conventionally, in the medical field and industrial fields, endoscope apparatuses in which an elongated insertion portion is inserted into an object and an image of a subject in the object is photographed by an imaging element provided in a distal end portion located at the distal end of the insertion portion are widely used. For example, in the field of medical use, medical endoscope apparatuses in which an insertion portion is inserted into a body cavity to observe an internal organ or the like in the body cavity, and various treatments are performed using a treatment tool inserted into a treatment instrument channel as necessary are used. For example, in industrial fields, industrial endoscope apparatuses are used for observing and inspecting internal scratches and corrosion of boilers, turbines, engines, chemical plants and the like.

For example, in aircraft engines, high-pressure turbine blades are parts that are susceptible to cracks and the like due to thermal shock, as high-pressure, high-temperature combustion air is sprayed. Damage such as cracks generated in such blades is fatal damage to the engine. Therefore, inspection and checking of blades of a high pressure turbine using an industrial endoscope apparatus is one of the most important items in maintenance of an aircraft engine. In the maintenance of the engine of the aircraft, in the inspection of the blade, the shape of the damage is measured, and whether or not to replace the blade is determined based on the measurement result.

At this time, in the inspection using the industrial endoscope apparatus, there are cases in which it is difficult to bring the distal end close to the vicinity of the measurement target due to the complicated structure of the object into which the insertion portion is inserted. In such a case, measurement may be performed by enlarging the image of the subject using the zoom function provided in the industrial endoscope apparatus. The zoom function of the industrial endoscope apparatus used at this time is a so-called electronic zoom function which cuts out a part of the region of the image of the photographed subject and enlarges the subject by image processing. However, although the electronic zoom can easily be used to inspect the subject in an enlarged state, there is a problem that the image quality deteriorates as the zoom magnification increases. This is because the number of pixels of the imaging element provided in the distal end portion does not change, and increasing the magnification of the zoom means that the area to cut out when forming the image of the subject becomes narrower, and thereby the number of pixels is reduced. If the inspection is performed in a state where the image quality is deteriorated, the inspection accuracy is lowered. Therefore, in an inspection using an industrial endoscope apparatus, in order to suppress degradation of image quality when the magnification of the zoom is increased, exchanging an objective lens for forming an image of a subject on an imaging element provided in the distal end portion for a lens with a high magnification is considered. However, when the objective lens is exchanged for a lens with a high magnification, it is necessary to draw out and replace the insertion portion inserted into the object to be inspected, and thus the inspection becomes complicated.

Incidentally, for example, Japanese Unexamined Patent Application, First Publication No. 2010-128354 (hereinafter referred to as Patent Document 1) proposes a configuration of an endoscope apparatus having two optical systems in its distal end portion. In the endoscope apparatus disclosed in Patent Document 1, an image of a subject corresponding to a right eye imaged by an optical system composed of an objective lens and an image of the subject corresponding to a left eye imaged by an optical system composed of the other objective lens are formed by one imaging element, and stereoscopic measurement is performed based on a three-dimensional image generated using the parallax of each image. In order for only light from one of the optical paths of the two optical systems to be incident on one imaging element, the endoscope apparatus disclosed in Patent Document 1 includes a divided optical path switching means for shielding the light from the other optical path. With this configuration, in the endoscope apparatus disclosed in Patent Document 1, the distal end portion can be made thinner as compared with the configuration in which the imaging element corresponding to each objective lens, that is, the two imaging elements, are provided at the distal end portion. In addition, Patent Document 1 discloses a configuration in which a wide range of measurement and enlarged measurement are performed by configuring the two optical systems with a variable magnification optical system. Therefore, by using the technique disclosed in Patent Document 1, by making one optical system into a wide angle optical system and the other optical system into a telephoto optical system, it is possible to realize an industrial endoscope apparatus which can perform inspection with two steps of optical magnification. Moreover, in the industrial endoscope apparatus realized by using the technique disclosed in Patent Document 1, it is possible to photograph the subject by using the objective lens of high magnification, without pulling out the insertion portion inserted into the object to be examined to exchange the objective lens.

Further, even if an industrial endoscope apparatus capable of photographing with two-step optical magnification is realized by using the technique disclosed in Patent Document 1, it is desirable for the electronic zoom function to be able to be used together. This is because when examination is performed by an industrial endoscope apparatus, magnification necessary for examination is not necessarily in two steps due to various factors such as the relationship of the distance between the subject and the distal end portion. Even when the inspection is performed using the electronic zoom in the industrial endoscope apparatus, it is desirable to switch the optical system at an appropriate zoom magnification in order to suppress deterioration of the inspection accuracy.

SUMMARY

An aspect of the present invention is an endoscope apparatus including: an insertion portion formed so as to extend in a longitudinal direction along a predetermined central axis and having a distal end portion; an optical path switching unit that is disposed inside the insertion portion and is configured to switch an optical path so that only one of a first subject image and a second subject image is imaged on an image forming area where the first subject image and the second subject image are commonly focused, the first subject image being an image of a subject formed by light emitted from a first objective optical system disposed at the distal end portion, the second subject image being an image of the subject formed by light emitted from a second objective optical system disposed at the distal end portion and having an optical magnification higher than that of the first objective optical system; an imaging element configured to generate an image acquired by picking up the first subject image and the second subject image formed in the image forming area; and an endoscope processing unit configured to control switching of the optical path based on an input zoom magnification and apply image processing to the image generated by the imaging element.

The endoscope processing unit may be configured to cause the optical path to be switched to an optical path on which the second subject image is formed when the zoom magnification is equal to or greater than an optical magnification of the second objective optical system, and to cause the optical path to be switched to an optical path on which the first subject image is formed when the zoom magnification is lower than the optical magnification of the second objective optical system.

The endoscope processing unit may be configured to change parameters of the image processing based on switching of the optical path.

The endoscope processing unit may be configured to perform image processing of electronic zoom for enlarging the image.

In the image processing of the electronic zoom, the image may be enlarged at an electronic zoom magnification based on the zoom magnification.

The endoscope processing unit may be configured to change the electronic zoom magnification based on switching of the optical path.

The endoscope processing unit may be configured to set a magnification acquired by dividing the zoom magnification by an optical magnification of the second objective optical system as the electronic zoom magnification when the optical path is switched to an optical path on which the second subject image is formed, and to set the zoom magnification as the electronic zoom magnification when the optical path is switched to an optical path on which the first subject image is formed.

The endoscope processing unit may be configured to set a center position of the image of the second subject image as a center position of the image to be enlarged in image processing of the electronic zoom.

The endoscope processing unit may be configured to perform image processing of shading correction for correcting shading appearing in the image.

In the image processing of the shading correction, each of shading appearing in the captured image of the first subject image and shading appearing in the captured image of the second subject image may be corrected to be a common correction target value.

The endoscope processing unit may be configured to switch a gain value for setting the correction target value based on switching of the optical path.

The endoscope processing unit may be configured to perform image processing of brightness correction for correcting the overall brightness of the image.

In the image processing for the brightness correction, a first area at a center portion of the image and a second area at a peripheral portion of the image may be set based on the zoom magnification, a brightness of the first region may be corrected with high weighting, and a brightness of the second region may be corrected with low weighting.

The endoscope processing unit may be configured to switch each weighting gain value corresponding to the first region and the second region based on switching of the optical path and the zoom magnification.

The endoscope processing unit may be configured to output an optical path switching drive signal to the optical path switching unit when switching the optical path, and the optical path switching unit may be configured to cause a light shielding member that shields one of the optical paths to slide by a magnetic field generated based on a polarity of a current in the optical path switching drive signal and to switch the optical path.

The insertion portion may include: a scope portion including a soft cord portion; and an optical adapter detachably attached to a distal end side of the scope portion. The first objective optical system, the second objective optical system, and the optical path switching unit may be disposed within the optical adapter. The imaging element may be disposed on the distal end side of the scope portion.

The endoscope processing unit may be configured to notify of switching of the optical path.

An aspect of the present invention is a control method of an endoscope apparatus, wherein the endoscope apparatus includes: an insertion portion formed so as to extend in a longitudinal direction along a predetermined central axis and having a distal end portion; an optical path switching unit that is disposed inside the insertion portion and is configured to switch an optical path so that only one of a first subject image and a second subject image is imaged on an image forming area where the first subject image and the second subject image are commonly focused, the first subject image being an image of a subject formed by light emitted from a first objective optical system disposed at the distal end portion, the second subject image being an image of the subject formed by light emitted from a second objective optical system disposed at the distal end portion and having an optical magnification higher than that of the first objective optical system; an imaging element configured to generate an image acquired by picking up the first subject image and the second subject image formed in the image forming area; and an endoscope processing unit configured to control switching of the optical path based on an input zoom magnification and apply image processing to the image generated by the imaging element. The control method includes: causing, by the endoscope processing unit, the optical path to be switched to an optical path on which the second subject image is formed when the zoom magnification is a magnification greater than or equal to an optical magnification of the second objective optical system; and causing, by the endoscope processing unit, the optical path to be switched to an optical path on which the first subject image is formed when the zoom magnification is a magnification lower than the optical magnification of the second objective optical system.

An aspect of the present invention is a computer-readable recording medium storing a control program of an endoscope apparatus, wherein the endoscope apparatus includes: an insertion portion formed so as to extend in a longitudinal direction along a predetermined central axis and having a distal end portion; an optical path switching unit that is disposed inside the insertion portion and is configured to switch an optical path so that only one of a first subject image and a second subject image is imaged on an image forming area where the first subject image and the second subject image are commonly focused, the first subject image being an image of a subject formed by light emitted from a first objective optical system disposed at the distal end portion, the second subject image being an image of the subject formed by light emitted from a second objective optical system disposed at the distal end portion and having an optical magnification higher than that of the first objective optical system; an imaging element configured to generate an image acquired by picking up the first subject image and the second subject image formed in the image forming area; and an endoscope processing unit configured to control switching of the optical path based on an input zoom magnification and apply image processing to the image generated by the imaging element. The control program causes a computer of the endoscope apparatus to execute: a process of causing the optical path to be switched to an optical path on which the second subject image is formed when the zoom magnification is a magnification greater than or equal to an optical magnification of the second objective optical system; and a process of causing the optical path to be switched to an optical path on which the first subject image is formed when the zoom magnification is a magnification lower than the optical magnification of the second objective optical system.

DETAILED DESCRIPTION OF THE PREFERRED EMBODIMENTS

First Embodiment

Figure 1:
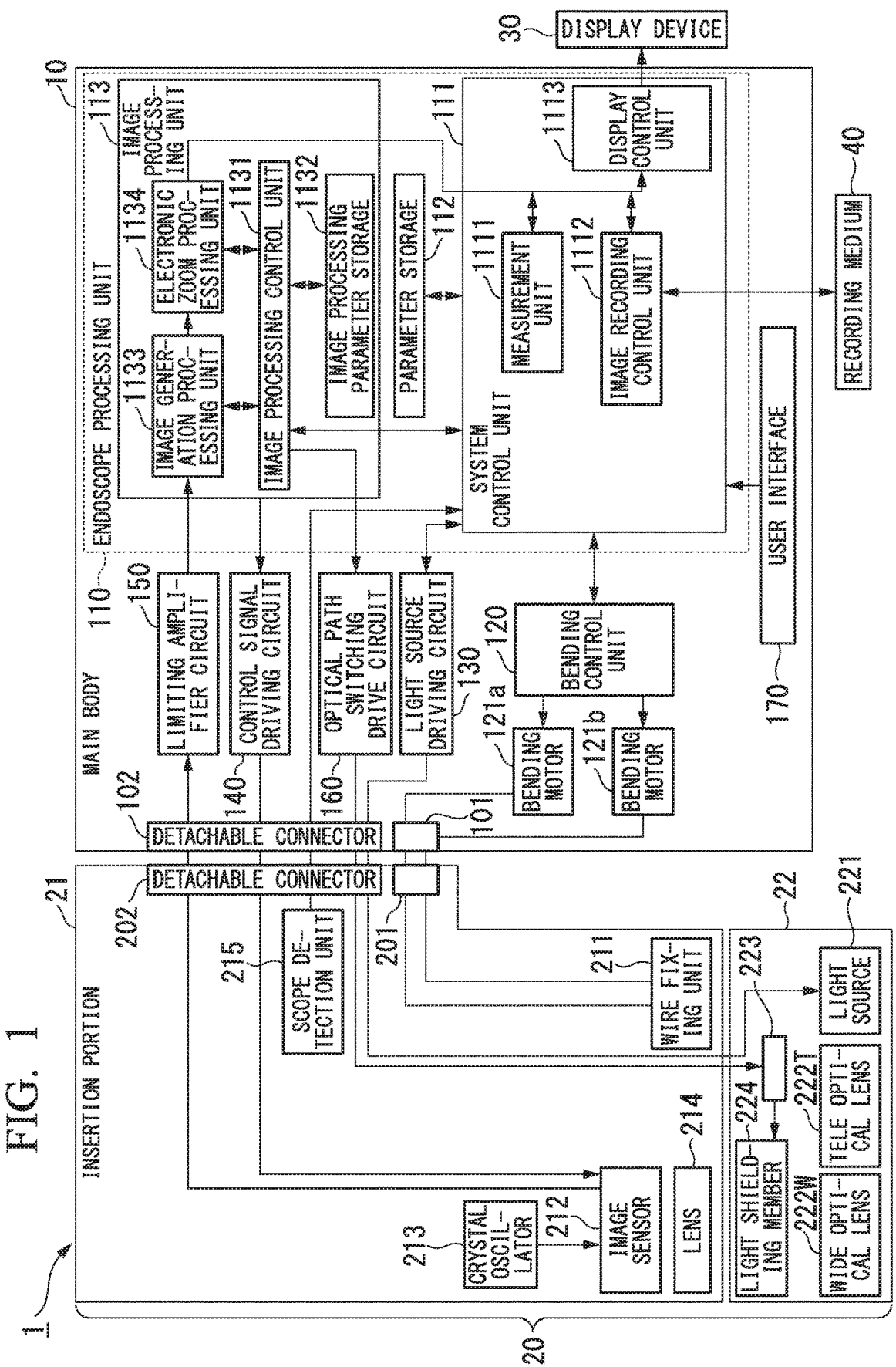
FIG. 1 is a block diagram showing an example of a configuration of an endoscope apparatus according to a first embodiment of the present invention.

Hereinafter, embodiments of the present invention will be described with reference to the drawings. In the following description, the case where the endoscope apparatus of the first embodiment is an industrial endoscope apparatus will be described. FIG. 1 is a block diagram showing an example of a configuration of an endoscope apparatus according to a first embodiment of the present invention. The endoscope apparatus 1 shown in FIG. 1 includes a main body 10 and an elongated insertion portion 20. In addition, in the endoscope apparatus 1 shown in FIG. 1, the display device 30 and the recording medium 40 are connected to the main body 10.

In the endoscope apparatus 1, a distal end side (hereinafter referred to as "distal end portion") of a soft insertion portion 20 having a shape extending in a longitudinal direction along a predetermined central axis is inserted into an object. Then, in the endoscope apparatus 1, a pixel signal representing a subject image in the object acquired by photographing by an imaging element disposed at the distal end portion is transmitted to the main body 10 connected to the proximal end side of the insertion portion 20. In the endoscope apparatus 1, the movement and direction of the distal end portion when the insertion portion 20 is inserted into the object to be inspected and the operation of photographing the subject by the imaging element disposed at the distal end portion are controlled by the main body 10.

In the endoscope apparatus 1, the pixel signal transmitted from the insertion portion 20 is processed in the main body 10, and an image (video) of the subject in the object is generated. The endoscope apparatus 1 displays the generated image (video) of the subject on the connected display device 30. The display device 30 displays an image of the subject in the object photographed by the endoscope apparatus 1. The display device 30 is, for example, a liquid crystal display (LCD) or the like. In FIG. 1, the display device 30 is shown as an external component connected to the main body 10, that is, as an external display device that is detachable from the main body 10, but the display device 30 may be a mounted component provided on the main body 10.

Further, in the endoscope apparatus 1, an image (video) of the subject generated by the main body 10 is recorded on the connected recording medium 40. The recording medium 40 records data of an image of the subject in the object photographed by the endoscope apparatus 1. The recording medium 40 has a configuration that is detachable from the main body 10, such as an SD memory card or a USB (Universal Serial Bus (registered trademark)) memory. In FIG. 1, the recording medium 40 is shown as an external recording medium that is detachable from the main body 10, but the recording medium 40 may be a component built in the main body 10, such as a storage device like a hard disk.

When the inside of the object is not photographed in the endoscope apparatus 1, for example, a flexible cord portion in the insertion portion 20 for guiding the imaging element disposed at the distal end portion into the inside of the object may be wound around a drum portion (not shown) attached to the main body 10 to be stored.

The main body 10 includes an endoscope processing unit 110, a bending control unit 120, two bending motors 121a and 121b, a light source driving circuit 130, a control signal driving circuit 140, a limiting amplifier circuit 150, an optical path switching drive circuit 160, a user interface 170, a wire connection mechanism 101, and a detachable connector 102. Further, the endoscope processing unit 110 includes a system control unit 111, a parameter storage 112, and an image processing unit 113. Further, the system control unit 111 includes a measurement unit 1111, an image recording processing unit 1112, and a display control unit 1113. The image processing unit 113 includes an image processing control unit 1131, an image processing parameter storage 1132, an image generation processing unit 1133, and an electronic zoom processing unit 1134.

The insertion portion 20 is configured to include a scope portion 21 having a flexible cord section and an optical adapter 22 detachably attached to the distal end side of the scope portion 21. The scope portion 21 includes a wire fixing unit 211, an image sensor 212, a crystal oscillator 213, a lens 214, a scope detection unit 215, a wire connection mechanism 201, and a detachable connector 202. Further, the optical adapter 22 includes a light source 221, a WIDE optical lens 222W, a TELE optical lens 222T, an optical path switching unit 223, and a light shielding member 224. In the scope portion 21, the wire fixing section 211, the image sensor 212, the crystal oscillator 213, and the lens 214 are disposed on the distal end side where the optical adapter 22 is mounted. In the following description, the distal end side of the scope portion 21 where the image sensor 212 and the like are disposed and the optical adapter 22 attached to the distal end side of the scope portion 21 are referred to as a "distal end portion" of the insertion portion 20.

Here, each component included in the endoscope apparatus 1 will be described in detail. First, each component provided in the optical adapter 22, which is attached to the distal end side of the scope portion 21 and constitutes the distal end portion of the insertion portion 20, will be described in detail.

The optical adapter 22 is an adapter of an optical system that causes light of the subject image in the object to be incident on the image sensor 212 disposed on the distal end side of the scope portion 21. It should be noted that the optical adapter 22 is a wide-angle telephoto switching adapter that photographs the subject to be measured by the endoscope apparatus 1 in the object at a wide angle (WIDE) or a telephoto (TELE).

The light source 221 emits light to be radiated onto the subject in the object. The light source 221 emits light at the light amount and the timing according to the drive signal output from the main body 10 and transmitted by the signal line in the scope portion 21. The light source 221 is, for example, a white LED (Light Emitting Diode) light source or the like.

Each of the WIDE optical lens 222W and the TELE optical lens 222T is an optical lens (objective lens) that emits incident light, that is, reflected light from the subject irradiated with light emitted by the light source 221, to the side of the image sensor 212, and forms a subject image on the image sensor 212. Each of the WIDE optical lens 222W and the TELE optical lens 222T is an optical lens that forms an image of reflected light from the subject in the same (common) imaging area. For example, each of the WIDE optical lens 222W and the TELE optical lens 222T forms an image of reflected light from the subject on the entire imaging area of the image sensor 212. However, the WIDE optical lens 222W and the TELE optical lens 222T have different optical magnifications. More specifically, the WIDE optical lens 222W is a wide-angle optical lens for photographing and measuring the subject at a wide angle in the endoscope apparatus 1, and the TELE optical lens 222T is a telephoto optical lens for enlarging the subject to be photographed and measured in the endoscope apparatus 1. For example, the optical magnification of the WIDE optical lens 222W is 1, and the optical magnification of the TELE optical lens 222T is 2 or 3. In the following description, the WIDE optical lens 222W and the TELE optical lens 222T are simply referred to as "optical lens 222" when they are not distinguished from each other.

The light shielding member 224 is a light shielding plate that shields the reflected light from the subject emitted from the WIDE optical lens 222W and the TELE optical lens 222T to the side of the scope portion 21. The light shielding member 224 is moved (slid) to either one of the optical path through which the WIDE optical lens 222W emits light or the optical path through which the TELE optical lens 222T emits light, by the optical path switching unit 223. Thereby, the reflected light from the subject emitted from either the WIDE optical lens 222W or the TELE optical lens 222T is emitted to the entire imaging area of the image sensor 212.

The optical path switching unit 223 is a mechanical mechanism (for example, an actuator, etc.) for switching the light incident on the image sensor 212 by moving (sliding) the light shielding member 224. When the light emitted from the WIDE optical lens 222W is made incident on the image sensor 212, the optical path switching unit 223 moves (slides) the light shielding member 224 on the optical path through which the TELE optical lens 222T emits light. Further, when the light emitted from the TELE optical lens 222T enters the image sensor 212, the optical path switching unit 223 moves (slides) the light shielding member 224 on the optical path through which the WIDE optical lens 222W emits light. That is, the optical path switching unit 223 moves (slides) the light shielding member 224 in either one of the optical path from which the WIDE optical lens 222W emits light or the optical path through which the TELE optical lens 222T emits light, thereby switching the light incident on the sensor 212. The optical path switching unit 223 moves (slides) the light shielding member 224 in accordance with the driving signal output from the main body 10 and transmitted by the signal line in the scope portion 21, and switches an optical path that emits the light to the image sensor 212 (in other words, an optical path that shields light by the light shielding member 224). As a result, the image sensor 212 captures the subject image at a wide angle or telephoto.

The configuration of the optical path switching unit 223 is, for example, a configuration in which a permanent magnet is fixed to a rotating shaft that rotates in a direction in which the light shielding member 224 moves (slides), and a coil is disposed around the permanent magnet. In the optical path switching unit 223 having this configuration, the light shielding member 224 is fixed to the rotating shaft, and a current having a polarity corresponding to the direction in which the rotating shaft is rotated is supplied to the coil as a driving signal. As a result, the coil generates a magnetic field (force field) corresponding to the polarity of the flowing current. The rotating shaft rotates in a direction corresponding to the polarity of the current flowing through the coil depending on the generated force field, and the light shielding member 224 fixed to the rotating shaft moves (slides). The optical path switching unit 223 is not limited to the above-described configuration, but may be configured such that the light shielding member 224 moves (slides) to either one of the optical path through which the WIDE optical lens 222W emits light or the optical path through which the TELE optical lens 222T emits light.

Next, each constituent element provided in the scope portion 21 constituting the insertion portion 20 will be described in detail.

In the state where the optical adapter 22 is attached to the distal end side, the scope portion 21 is inserted into the object from the distal end portion, and transmits a pixel signal representing the subject image that is formed by the reflected light from the subject in the object incident from the optical adapter 22, to the main body 10.

The wire fixing portion 211 is a mechanism for fixing one end of a bending wire for changing the movement and direction of the distal end side of the scope portion 21, that is, the distal end portion of the insertion portion 20, to the distal end side by the main body 10.

The lens 214 is a so-called relay lens that emits reflected light from the subject in the object incident from the optical adapter 22 to the side of the image sensor 212. The lens 214 is composed of a parallel flat lens or the like. The lens 214 allows the light of the optical path through which the WIDE optical lens 222W or the TELE optical lens 222T emits light to the image sensor 212 that is switched by the optical path switching unit 223 provided in the optical adapter 22 to be emitted to the entire imaging area of the image sensor 212.

The crystal oscillator 213 oscillates a clock signal of a predetermined frequency necessary when the image sensor 212 operates and supplies the oscillated clock signal to the image sensor 212.

The image sensor 212 is a CMOS (Complementary Metal-Oxide Semiconductor) image sensor that operates based on the clock signal supplied from the crystal oscillator 213. The image sensor 212 captures the subject image in the object in accordance with the control signal output from the main body 10. Then, the image sensor 212 transmits a pixel signal (for example, a RAW signal) representing the subject image in the inspected object to the main body 10 through a signal line in the cord portion. The image sensor 212 transmits a pixel signal of a captured subject image to the main body 10 by a transmission method such as SLVS-EC (Scalable Low Voltage Signaling with Embedded Clock) serial communication.

The wire connecting mechanism 201 is a mechanism by which the insertion portion 20 (more specifically, the scope portion 21) is detachably attached to the main body 10, and the bending wire fixed to the distal end side of the scope portion 21 by the wire fixing portion 211 is connected to a wire for changing the movement and direction of the distal end portion of the insertion portion 20 in the main body 10. In the following description, to facilitate the explanation, it is assumed that the bending wire connected by the wire connecting mechanism 201 and the wire on the side of the main body 10 are one wire, and the whole of the connected wires is referred to as a bending wire.

The detachable connector 202 is a mechanism by which the insertion portion 20 (more specifically, the scope portion 21) is detachably attached to the main body 10, and the respective constituent elements provided in the scope portion 21 and the optical adapter 22 and the correspondence constituent elements provided in the main body 10 are connected by a signal line. In the following description, for the sake of easy explanation, the signal line between the respective constituent elements provided in the scope portion 21 and the optical adapter 22 and the corresponding constituent elements provided in the main body 10 is one signal line.

The scope detection unit 215 outputs a detection signal indicating that the insertion portion 20 (more specifically, the scope portion 21) is attached to the main body 10 to the main body 10. When one end of the cord portion on the opposite side to the distal end side of the scope portion 21 is correctly connected to the main body 10 by the wire connection mechanism 201 and the detachable connector 202, the scope detection unit 215 outputs a detection signal indicating this to the main body 10.

Next, each component included in the main body 10 will be described in detail.

The main body 10 controls photographing and measurement of the subject in the object in the endoscope apparatus 1 according to an operation by a user of the endoscope apparatus 1.

The wire connecting mechanism 101 is a mechanism on the side of the main body 10 by which the insertion portion 20 (more specifically, the scope portion 21) is detachably attached to the main body 10 by fitting the wire connecting mechanism 101 with the wire connecting mechanism 201 provided in the scope portion 21, and the bending wire fixed by the wire fixing portion 211 is connected on the side of the distal end of the scope portion 21 as one wire.

The detachable connector 102 is a mechanism on the side of the main body 10 by which the insertion portion 20 (more specifically, the scope portion 21) is detachably attached to the main body 10 by fitting the detachable connector 102 with the detachable connector 202 provided in the scope portion 21, and the respective constituent elements provided in the scope portion 21 and the optical adapter 22 are connected to the corresponding constituent elements provided in the body part 10 by a single signal line.

The limiting amplifier circuit 150 is an amplifier circuit (amplifier) that amplifies the pixel signal of the subject image transmitted by the corresponding signal line from the image sensor 212 provided at the distal end portion of the insertion portion 20. The reason that the limiting amplifier circuit 150 is provided in the main body 10 is that, in the endoscope device 1, the length of the insertion portion 20 (more specifically, the scope portion 21) is very long (for example, ten meters), and therefore the pixel signal output from the image sensor 212 may be attenuated until it is transmitted to the main body 10 by the corresponding signal line. The limiting amplifier circuit 150 amplifies the signal level of the pixel signal output from the image sensor 212 to a signal level necessary for the image processing unit 113 provided in the endoscope processing unit 110 to perform image processing. Then, the limiting amplifier circuit 150 outputs the pixel signal acquired by amplifying the signal level to the image processing unit 113 in the endoscope processing unit 110.

The control signal drive circuit 140 is a drive circuit (drive circuit) for amplifying and outputting a control signal to the image sensor 212 output from the image processing unit 113 provided in the endoscope processing unit 110. The control signal drive circuit 140 amplifies the control signal output by the image processing unit 113 to a necessary signal level and outputs it so that the control signal is correctly input to the image sensor 212 disposed on the distal end side of the scope portion 21. More specifically, the control signal drive circuit 140 amplifies the current of the control signal output by the image processing unit 113 and outputs it to the image sensor 212. As a result, the image sensor 212 correctly receives the control signal output from the image processing unit 113, and performs the photographing operation in the operation mode or setting according to the received control signal.

The user interface 170 accepts an operation by a user of the endoscope apparatus 1. The user interface 170 outputs the received information representing the operation of the user of the endoscope apparatus 1 to the system control unit 111 provided in the endoscope processing unit 110. The user interface 170 is constituted by, for example, a dedicated operation device such as a remote control terminal equipped with a button, a switch, a joystick, and the like that are operated by the user. The user of the endoscope apparatus 1 instructs the movement and direction of the distal end portion when the distal end portion of the insertion portion 20 is inserted into the object by operating the user interface 170. Further, the user of the endoscope apparatus 1 instructs zooming when the subject is photographed in the endoscope apparatus 1, that is, magnification of zooming. Further, the user of the endoscope apparatus 1 instructs measurement and the like of the subject in the endoscope apparatus 1.

The bending control unit 120 generates a driving signal for actually controlling the movement and direction of the distal end portion of the insertion portion 20 based on the control signal (hereinafter referred to as a "bending control signal") output from the system control unit 111 provided in the endoscope processing unit 110 for controlling the movement and direction of the distal end portion of the insertion portion 20 (more specifically, the distal end side of the scope portion 21). More specifically, based on the bending control signal output from the system control unit 111 in the endoscope processing unit 110, the bending control unit 120 generates each of a drive signal for moving the distal end portion of the insertion portion 20 in the vertical direction and a drive signal for moving the distal end portion of the insertion portion 20 in the lateral direction. Then, the bending control unit 120 outputs the generated drive signals to the bending motor 121a and the bending motor 121b, respectively. For example, the bending control unit 120 outputs a drive signal for moving the distal end portion of the insertion portion 20 in the vertical direction (hereinafter referred to as "vertical drive signal") to the bending motor 121a, and outputs a drive signal for moving the distal end portion of the insertion portion 20 in the lateral direction (hereinafter referred to as "left and right driving signals") to the bending motor 121b. When the bending motor 121a and the bending motor 121b are driven with the corresponding driving signals, the bending control unit 120 performs feedback control based on the actual amount of movement of each of the bending motor 121a and the bending motor 121b. That is, the bending control unit 120 detects the amount of the actual movement of the bending wire and performs feedback control of the movement and direction of the distal end portion of the insertion portion 20.

Each of the bending motor 121a and the bending motor 121b is a motor that actually moves the distal end portion of the insertion portion 20 by pulling the corresponding bending wire in accordance with the corresponding driving signal output from the bending control unit 120. More specifically, each of the bending motor 121a and the bending motor 121b pulls either one of the two bending wires in the corresponding direction, and at the same time loosens the other bending wire (not initiatively pushed out). Thereby, the distal end portion of the insertion portion 20 is oriented in the direction instructed by the user of the endoscope apparatus 1 by operating the user interface 170. For example, when the bending motor 121a is a motor for moving the distal end portion of the insertion portion 20 in the vertical direction, based on the vertical drive signal output from the bending control unit 120, two bending wires are pulled as described above to actually move the distal end portion of the insertion portion 20 in the vertical direction. Further, for example, when the bending motor 121b is a motor for moving the distal end portion of the insertion portion 20 in the lateral direction, based on the left and right driving signal output from the bending control unit 120, the two corresponding bending wires are pulled in the lateral direction as described above, and the distal end portion of the insertion portion 20 is actually moved in the lateral direction. Each of the bending motor 121a and the bending motor 121b is provided with, for example, a potentiometer (not shown). The potentiometer (not shown) detects the actual amount of rotation by which the bending motor 121a and the bending motor 121b rotate in order to pull the bending wire in accordance with the corresponding driving signal. Information on the amount of rotation of each of the bending motor 121a and the bending motor 121b detected by the potentiometer is output to the bending control unit 120 and used for feedback control by the bending control unit 120.

The light source driving circuit 130 is a drive circuit that amplifies and outputs a drive signal (hereinafter referred to as "light emission drive signal") for controlling the light amount and timing of light emitted from the light source 221 provided at the distal end portion of the insertion portion 20 (more specifically, the optical adapter 22 attached to the distal end side of the scope portion 21), output from the system control unit 111 provided in the endoscope processing unit 110. The light source driving circuit 130 amplifies the light emitting drive signal output by the system control unit 111 in the endoscope processing unit 110 to a required signal level so as to be correctly input to the light source 221 in the optical adapter 22 mounted on the distal end side of the scope portion 21, thereby driving the light source driving circuit 130. Like the control signal drive circuit 140, the light source drive circuit 130 also amplifies current of the light emission drive signal output by the system control unit 111 and outputs it to the light source 221. Thus, the light source 221 emits light having a light amount corresponding to the light emission drive signal.

The optical path switching drive circuit 160 is a drive circuit for amplifying and outputting a drive signal (hereinafter referred to as "optical path switching drive signal") for controlling the movement (sliding) of the light shielding member 224 by the optical path switching unit 223 provided at the distal end portion of the insertion portion 20 (more specifically, the optical adapter attached to the distal end side of the scope portion 21), output from the image processing unit 113 provided in the endoscope processing unit 110. The optical path switching drive circuit 160 amplifies the optical path switching drive signal output from the image processing unit 113 in the endoscope processing unit 110 to the necessary signal level so that it is correctly input to the optical path switching unit 223 in the optical adapter 22 mounted on the distal end side of the scope portion 21, thereby driving optical path switching drive circuit 160. Similarly to the control signal drive circuit 140 and the light source drive circuit 130, the optical path switching drive circuit 160 also amplifies current of the optical path switching drive signal output by the image processing unit 113 and outputs it to the optical path switching unit 223. As a result, the optical path switching unit 223 switches the reflected light from the subject, which is emitted to the entire imaging area of the image sensor 212, to the reflected light from the subject emitted to the optical path of either one of the WIDE optical lens 222W or the TELE optical lens 222T, which is indicated by the optical path switching drive signal.

The endoscope processing unit 110 performs overall control and processing in the endoscope apparatus 1. The endoscope processing unit 110 is configured to include a processing device such as a CPU (Central Processing Unit). It is to be noted that the endoscope processing unit 110 may be configured to realize all functions or some functions as processors. At this time, the endoscope processing unit 110 may be configured to realize all the functions by one processor, or may be a configuration in which functions are realized by an individual processor corresponding to each function, that is, a plurality of processors. In addition, the endoscope processing unit 110 may be configured to realize all functions or a part of functions with a dedicated LSI (Large Scale Integration) in combination with a CPU, so-called ASIC (Application Specific Integrated Circuit) or the like. For example, the endoscope processing unit 110 may be configured to realize the function of the system control unit 111 by one processor, and realize the function of the image processing unit 113 by one ASIC.

In the endoscope processing unit 110, the system control unit 111 performs control related to the entire operation of the endoscope apparatus 1, and the image processing unit 113 performs control related to the photographing operation of the subject in the endoscope apparatus 1 and processing of generating an image (video) of the photographed subject.

The parameter storage 112 is a memory that stores a program for realizing the function of the system control unit 111 and setting value data. The parameter storage 112 includes various memories such as a ROM (Read Only Memory), an EPROM (Erasable Programmable Read Only Memory), a RAM (Random Access Memory), and a flash memory (Flash Memory).

The system control unit 111 is configured to include a processing device such as a CPU, reads programs and setting value data stored in the parameter storage 112 at the time of activation, and performs functions according to the read program and the setting value (initial value) data.

The system control unit 111 controls the movement and direction of the distal end portion of the insertion portion 20 according to the instruction of the movement or direction of the distal end portion input by the user of the endoscope apparatus 1 by operating the user interface 170. At this time, on the basis of the detection signal output from the scope detection unit 215 provided in the insertion portion 20 (more specifically, the scope portion 21), the system control unit 111 determines attachment/detachment of the insertion portion 20 to/from the main body 10. Then, when the insertion portion 20 is properly connected to the main body 10, the system control unit 111 outputs the bending control signal to the bending control unit 120 for controlling the movement and direction of the distal end portion of the insertion portion 20 (more specifically, the distal end side of the scope portion 21). Thus, the bending control unit 120 generates driving signals (a vertical driving signal and a left and right driving signal) corresponding to the bending motor 121*a* and the bending motor 121*b*, and the movement and the direction of the distal end portion of the insertion portion 20 are actually controlled.

Further, in accordance with the instruction of photographing input by the user of the endoscope apparatus 1 by operating the user interface 170, the system control unit 111 controls photographing of the subject in the object in the endoscope apparatus 1. For example, the system control unit 111 controls photographing of the subject with a zoom magnification according to an instruction of zoom input by a user of the endoscope apparatus 1 by operating the user interface 170. At this time, the system control unit 111 performs various settings relating to activation and photographing operation of the image sensor 212 provided at the distal end portion (more specifically, the distal end side of the scope portion 21) of the insertion portion 20 by a predetermined communication method such as UART (Universal Asynchronous Receiver-Transmitter) to the image processing unit 113. The setting related to the photographing operation output by the system control unit 111 to the image processing unit 113 includes information on the zoom magnification according to the zoom instruction by the user of the endoscope apparatus 1. Further, the system control unit 111 outputs a light emission drive signal for controlling the amount and timing of light emitted from the light source 221 provided in the distal end portion of the insertion portion 20 (more specifically, the optical adapter 22 attached to the distal end side of the scope portion 21) to the light source 221. At this time, the system control unit 111 acquires the control signal information output by the image processing unit 113 to the image sensor 212 from the image processing unit 113 by UART. In particular, the system control unit 111 acquires information on the operation timing of the image sensor 212 from the image processing unit 113. Based on the acquired information on the control signal, the system control unit 111 causes the light source 221 to emit light in synchronization with the operation timing of the image sensor 212, that is, in synchronization with the imaging timing of the subject image in the image sensor 212, to the light source 221. More specifically, the system control unit 111 outputs, to the light source 221, a light emission drive signal that controls the light source 221 to emit light during the exposure period during which the image sensor 212 captures the subject image. As described above, in the endoscope apparatus 1, the length of the insertion portion 20 (more specifically, the scope portion 21) is very long, and even if the system control unit 111 outputs the drive signal for driving the light source 221 directly to the light source 221, it is conceivable that the output light emission drive signal is attenuated by the corresponding signal line before it reaches the light source 221 provided in the optical adapter 22. Therefore, the system control unit 111 outputs the light emission drive signal to be output to the light source 221 to the light source drive circuit 130. As a result, the light source drive circuit 130 amplifies the light emission drive signal output from the system control unit 111 and outputs it to the light source 221, and the light source 221 emits light of a light amount corresponding to the light emission drive signal at the timing synchronized with the image sensor 212.

It should be noted that the configuration for causing the light source 221 in the optical adapter 22 mounted on the distal end side of the scope portion 21 to emit light is not limited to the above-described configuration. For example, a configuration in which the system control unit 111 outputs a control signal (hereinafter referred to as "light emission control signal") for controlling the light emission of the light source 221 to the light source drive circuit 130, and the light source drive circuit 130 generates and outputs a light emission drive signal for the light source 221 to emit at the light amount and timing of the light indicated by the emitted light control signal output from the system control unit 111 may be adopted.

Further, the system control unit 111 controls display on the display device 30 and recording on the recording medium 40 of an image (video) of the subject generated by the image processing unit 113 in accordance with a display or recording instruction input by a user of the endoscope apparatus 1 by operating the user interface 170. More specifically, the display control unit 1113 provided in the system control unit 111 causes the display device 30 to display the image (video) of the subject generated by the image processing unit 113. Further, the image recording processing unit 1112 provided in the system control unit 111 causes the recording medium 40 to record the image (video) of the subject generated by the image processing unit 113.

The display control unit 1113 performs control for causing the display device 30 to display the image (video) of the subject generated by the image processing unit 113. More specifically, the display control unit 1113 converts the image (video) of the subject generated by the image processing unit 113 into the format and the image size of the display image to be displayed on the display device 30, and outputs the converted image to the display device 30 to display it. Further, the display control unit 1113 controls display of an on-screen display (OSD) image, which shows various information in the display image, such as an operation menu of the endoscope apparatus 1 and a measurement result of the subject, superimposed on the display image to be displayed on the display device 30.

The image recording processing unit 1112 performs control for causing the recording medium 40 to record the image (video) of the subject generated by the image processing unit 113. More specifically, the image recording processing unit 1112 converts the image (video) of the subject generated by the image processing unit 113 into a format of a recorded image to be recorded on the recording medium 40, and outputs the converted image to the recording medium 40 to record it. Note that formats of the recorded image converted by the image recording processing unit 1112 include a still image compression format such as JPEG, a moving image compression format such as MPEG, and the like.

In the endoscope apparatus 1, measurement of input items is performed using the captured image of the subject within the object, by the user of the endoscope apparatus 1 operating the user interface 170. In the system control unit 111, the measurement unit 1111 performs measurement based on the image (video) of the subject generated by the image processing unit 113.

The measurement unit 1111 is a processing unit that performs measurement based on the image (video) of the subject generated by the image processing unit 113. For example, when measuring the size (length) of the subject in the endoscope apparatus 1, the user of the endoscope apparatus 1 designates two points to measure the length by operating the user interface 170. The measurement unit 1111 measures the distance between the two designated points based on the image (video) of the subject generated by the image processing unit 113 and the zoom magnification. Since the measurement method and the like when the measurement unit 1111 performs measurement are the same as the existing measurement method, the detailed description is omitted. Then, the measurement unit 1111 outputs the information on the result of measurement using the image of the photographed subject to the display control unit 1113. As a result, the display control unit 1113 superimposes the on-screen display image for indicating the information of the result measured by the measuring unit 1111 on the display image, and displays the on-screen display image on the display device 30. In addition, the measurement unit 1111 outputs information on the result of measurement using the captured image of the subject to the image recording processing unit 1112. As a result, the image recording processing unit 1112 associates the information of the result measured by the measuring unit 1111 with the recorded image and records it on the recording medium 40.

As described above, in the endoscope processing unit 110, the image processing unit 113 performs processing related to the photographing operation of the subject in the endoscope apparatus 1 and generation processing of the captured image of the subject (video).

The image processing unit 113 outputs a control signal for controlling the image sensor 212 to the image sensor 212 based on various settings relating to activation of the image sensor 212 set by the system control unit 111 and operations of photographing. The control signal output to the image sensor 212 by the image processing unit 113 includes a setting value of a register for setting an operation mode and the like in the image sensor 212. The image processing unit 113 outputs control signals to the image sensor 212 using various predetermined serial communication methods such as I2C (Inter-Integrated Circuit) and SPI (Serial Peripheral Interface), for example. As described above, in the endoscope apparatus 1, the length of the insertion portion 20 (more specifically, the scope portion 21) is very long, and it is conceivable that the output control signal is attenuated by the corresponding signal line before it reaches the image sensor 212 arranged on the distal end side of the scope portion 21 even if the image processing unit 113 outputs the control signal for controlling the image sensor 212 directly to the image sensor 212. Therefore, the image processing unit 113 outputs a control signal to be output to the image sensor 212 to the control signal drive circuit 140. As a result, the control signal drive circuit 140 amplifies the control signal output from the image processing unit 113 and outputs it to the image sensor 212, and the image sensor 212 amplifies the subject according to the control signal output from the image processing unit 113. Further, the image processing unit 113 generates an image (video) of the subject in the object based on the pixel signal (for example, the RAW signal) of the subject image photographed and output by the image sensor 212 according to the output control signal.

The image processing parameter storage 1132 is a storage device that stores setting value data for realizing the image processing function in the image processing unit 113. The image processing parameter storage 1132 is composed of registers. The image processing parameter storage 1132 may include various memories such as a ROM, an EPROM, a RAM, a flash memory, and the like. It should be noted that the image processing parameter storage 1132 may store a program for realizing the function of the image processing unit 113. When the image processing control unit 1131 is configured to include a processing device such as a CPU, the image processing control unit 1131, at the time of activation, reads data of programs and setting values stored in the image processing parameter storage 1132 and performs an operation according to the read program and setting value (initial value) data.

The image processing control unit 1131 performs the photographing operation by the image sensor 212 and the operation of generating the image (video) of the subject by the image generation processing unit 1133 according to the settings relating to the photographing operation set by the UART by the system control unit 111.

The image generation processing unit 1133 is a digital signal processing unit that performs various predetermined types of image processing on the pixel signal (for example, RAW signal) of the subject image output from the image sensor 212 in the distal end portion output from the limiting amplifier circuit 150 and generates a captured image (video) of the subject in the object. Here, the image processing performed by the image generation processing unit 1133 is to convert the pixel signal of the subject image output by the image sensor 212 into an image signal (image data) of a general image format such as YUV 422, which is so-called development processing. For example, when the color array of the color filter attached to each pixel arranged in the imaging region of the image sensor 212 is a Bayer array, in the development processing, the image generation processing unit 1133 performs a three-paneling process (demosaicking process) or the like of conversion into a luminance signal or a color signal representing an image (video) of the subject on the basis of the information of each pixel included in the pixel signal output by the image sensor 212. Further, the image generation processing unit 1133 performs signal processing such as gamma correction processing, contour correction processing, color correction processing, and the like, on the demosaicked image signal (image data). The image generation processing unit 1133 outputs the image (video) of the subject generated from the pixel signal output by the image sensor 212 by the development processing to the electronic zoom processing unit 1134. The processing method of the demosaicking process (three-paneling process) in the image generation processing unit 1133 is similar to the processing method of the existing demosaicking process (three-paneling process), and therefore a detailed description thereof will be omitted. The respective processing methods of the gamma correction processing, the contour correction processing, and the color correction processing in the image generation processing unit 1133 are the same as the respective processing methods of the existing gamma correction processing, the contour correction processing, and the color correction processing, and therefore a detailed explanation will be omitted.

Further, the image processing control unit 1131 controls the electronic zoom operation by the electronic zoom processing unit 1134 according to the information of the zoom magnification included in the setting related to the photographing operation set by the UART by the system control unit 111.

The electronic zoom processing unit 1134 is a digital signal processing unit that generates an enlarged image (video) of the subject by applying electronic zoom processing to the image (video) of the subject output from the image generation processing unit 1133. The electronic zoom processing unit 1134 generates the final image (video) of the subject enlarged to the zoom magnification output from the image processing control unit 1131. For example, the electronic zoom processing unit 1134 cuts out an area corresponding to the zoom magnification in the image (video) of the subject generated by the image generation processing unit 1133, and enlarges it so that the cut-out area becomes the entire area of the image (video) of the subject to generate a new (final) image (video) of the subject. The electronic zoom processing unit 1134 outputs the final image (video) of the subject generated by performing the electronic zoom processing to the system control unit 111. Since the electronic zoom processing method in the electronic zoom processing unit 1134 is similar to the existing electronic zoom processing method, a detailed description thereof will be omitted.

In the endoscope apparatus 1, depending on the configuration of the insertion portion 20 described above, that is, the configuration of the optical adapter 22 attached to the distal end portion of the scope portion 21, it is possible to photograph the subject in the object at two levels of optical magnification. Therefore, when photographing the subject at the magnification corresponding to the zoom instruction input by the user of the endoscope apparatus 1 operating the user interface 170, the image processing control unit 1131 controls the operation of electronic zoom by the electronic zoom processing unit 1134 and the operation of switching the optical lens 222 provided in the optical adapter 22. More specifically, when the zoom magnification instructed by the user of the endoscope apparatus 1 is within the range of the predetermined zoom magnification, the image processing control unit 1131 causes the electronic zoom processing unit 1134 to perform the electronic zoom processing. On the other hand, when the zoom instructed by the user of the endoscope apparatus 1 exceeds the predetermined zoom magnification, the image processing control unit 1131 switches the optical path of the optical lens 222 provided in the optical adapter 22, and then causes the electronic zoom processing unit 1134 to continue the electronic zoom processing. That is, the image processing control unit 1131 sets the zoom magnification when the electronic zoom processing unit 1134 performs the electronic zoom processing on the image (video) of the subject photographed with the WIDE optical lens 222W for wide angles as the optical magnification of the TELE optical lens 222T for telephoto. When the zoom magnification instructed by the user of the endoscope apparatus 1 exceeds the optical magnification of the TELE optical lens 222T, the image processing control unit 1131 switches the imaging of the subject by the TELE optical lens 222T, and then causes the electronic zoom processing unit 1134 to perform the subsequent electronic zoom processing. In other words, when deterioration of image quality caused by electronic zoom processing performed by the electronic zoom processing unit 1134 on the image (video) of the subject photographed by the WIDE optical lens 222W exceeds a predetermined range, the image processing control unit 1131 switches the operation to photographing of the subject by the TELE optical lens 222T. As a result, even when the electronic zoom processing unit 1134 generates an image (video) of the subject with the same zoom magnification according to an instruction from the user of the endoscope apparatus 1, it is possible to lower the zoom magnification that is magnified by the electronic zoom processing and to reduce the influence of degradation of image quality due to electronic zooming. For example, when the optical magnification of the WIDE optical lens 222W is 1 times and the optical magnification of the TELE optical lens 222T is 2 times, a case of generating a final image (video) of the subject with a zoom magnification of 6 times is assumed. In this case, the image quality of the final image (video) of the subject that is made by enlarging the image (video) of the subject, which is doubly magnified optically by the TELE optical lens 222T, to a zoom magnification of 3 times by the electronic zoom processing by the electronic zoom processing unit 1134 is lower than that of the final image (video) of the subject that is enlarged to a zoom magnification of 6 times only by the electronic zoom processing by the electronic zoom processing unit 1134. Thus, in the endoscope apparatus 1, degradation in image quality of an image (video) of the final photographed subject can be reduced even when enlarged to the same zoom magnification.

When switching the optical lens 222 provided in the optical adapter 22, the image processing control unit 1131 switches the optical path for emitting light to the image sensor 212 by the optical path switching unit 223 provided in the optical adapter 22 so that reflected light from the subject emitted from either one of the WIDE optical lens 222W or the TELE optical lens 222T is emitted to the entire imaging area of the image sensor 212. At this time, the image processing control unit 1131 outputs to the optical path switching unit 223 an optical path switching driving signal for the optical path switching unit 223 to control the movement (sliding) of the light shielding member 224. As described above, in the endoscope apparatus 1, the length of the insertion portion 20 (more specifically, the scope portion 21) is very long, and it is conceivable that, even if the image processing control unit 1131 outputs the optical path switching drive signal for switching the optical path of the reflected light from the subject incident on the image sensor 212 directly to the optical path switching unit 223, the output optical path switching drive signal is attenuated by the corresponding signal line before it reaches the optical path switching unit 223 provided in the optical adapter 22. Therefore, the image processing control unit 1131 outputs the optical path switching drive signal to be output to the optical path switching unit 223 to the optical path switching drive circuit 160. Thereby, the optical path switching drive circuit 160 amplifies the optical path switching drive signal output from the image processing control unit 1131 and outputs it to the optical path switching unit 223, and the optical path switching unit 223 moves (slides) the light shielding member 224 in one of the optical paths of the optical path through which the WIDE optical lens 222W emits light or the optical path through which the TELE optical lens 222T emits light in accordance with the optical path switching drive signal output from the image processing control unit 1131. As a result, the optical path of the reflected light from the subject incident on the image sensor 212 is switched to the optical path of either the WIDE optical lens 222W or the TELE optical lens 222T.

Note that the configuration for switching the optical path of the reflected light from the subject incident on the image sensor 212 by the optical path switching unit 223 in the optical adapter 22 attached to the distal end side of the scope portion 21 is not limited to the configuration described above. For example, a configuration in which the image processing control unit 1131 outputs a control signal (hereinafter referred to as "optical path switching control signal") for controlling the switching of the optical path of the reflected light from the subject incident on the image sensor 212 to the optical path switching drive circuit 160, and the optical path switching drive circuit 160 generates an optical path switching drive signal for switching to the optical path of the optical lens 222 represented by the optical path switching control signal output from the image processing control unit 1131 and outputs it to the optical path switching unit 223 may be adopted.

Note that the image processing control unit 1131 notifies the system control unit 111 of the output of the optical path switching drive signal to the optical path switching unit 223, for example, by UART. More specifically, the image processing control unit 1131 outputs to the system control unit 111 information indicating that the optical path for causing the reflected light from the subject to be incident on the image sensor 212 is switched to either the optical path of the WIDE optical lens 222W or the optical path of the TELE optical lens 222T. As a result, the system control unit 111 can control the display control unit 1113 so as to superimpose the information representing the switched optical lens 222 as an on-screen display image when causing the image processing unit 113 (more specifically, the electronic zoom processing unit 1134) to display the final image (video) of the subject generated at the instructed zoom magnification on the display device 30.

Figure 2:
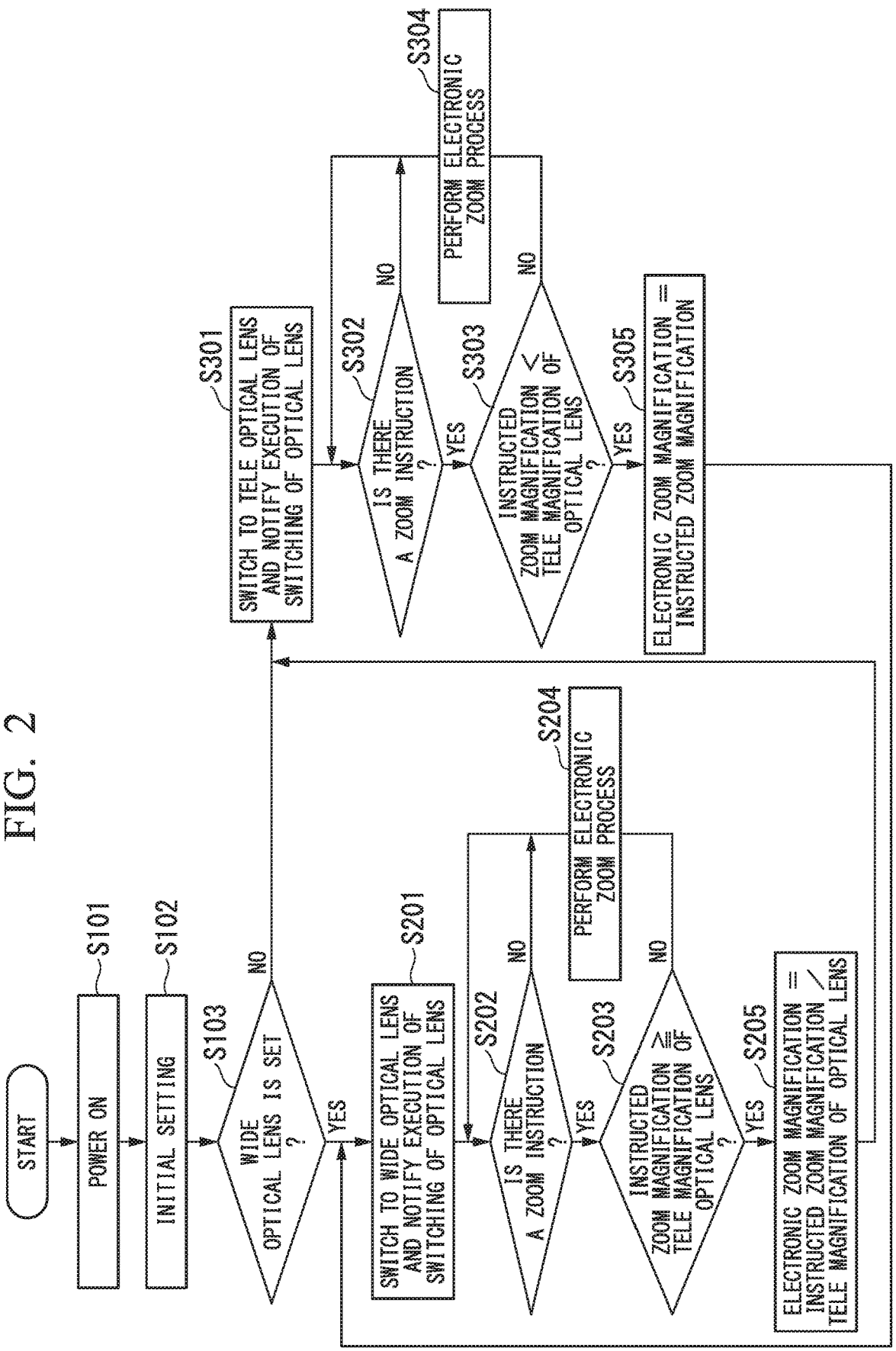
FIG. 2 is a flowchart showing an example of a procedure of zoom control in the endoscope apparatus according to the first embodiment of the present invention.

Next, a control method for zooming in the endoscope apparatus 1 of the first embodiment will be described. FIG. 2 is a flowchart showing an example of a zoom control processing procedure in the endoscope apparatus 1 according to the first embodiment of the present invention. FIG. 2 shows a method of controlling zooming when the image processing control unit 1131 provided in the image processing unit 113 in the endoscope processing unit 110 of the main body 10 photographs the subject.

When the power is turned on with the optical adapter 22 attached to the distal end side of the scope portion 21, the main body 10 is activated (step S101). As a result, the system control unit 111 provided in the endoscope processing unit 110 in the main body 10 reads the program and setting value data stored in the parameter storage 112, and starts the operation of the function corresponding to the read program and read setting value (initial value) data. Then, the system control unit 111 sets up the image processing unit 113 regarding activation and operation relating to photographing of the image sensor 212.

Subsequently, the image processing unit 113 provided in the endoscope processing unit 110 in the main body 10 reads the data of the setting value stored in the image processing parameter storage 1132, and performs the initial setting of the components in the insertion portion 20 and the image processing unit 113 in accordance with the read setting value (initial value) data (step S102). More specifically, the image processing unit 113 outputs an initial setting control signal of the image sensor 212 in the distal end portion of the insertion portion 20 to the image sensor 212 via the control signal drive circuit 140 and the corresponding signal line. Further, the image processing control unit 1131 provided in the image processing unit 113 sets parameters of the image generation processing unit 1133. Further, the image processing control unit 1131 sets the zoom magnification when the electronic zoom processing unit 1134 performs the electronic zoom processing as 1 times. In the image processing parameter storage 1132, for example, when the endoscope apparatus 1 starts measurement of the subject to be measured in the object, information on the optical lens 222 used for the first time or the like is stored in an endoscope in advance by the user of the endoscope apparatus 1. For this reason, in the initial setting process in step S102, the image processing control unit 1131 provided in the image processing unit 113 first outputs the optical path switching drive signal for switching to the optical path of the optical lens 222 that emits light to the image sensor 212 to the optical path switching unit 223 via the optical path switching drive circuit 160 and the corresponding signal line. Thereby, in response to the optical path switching drive signal output from the image processing control unit 1131, the optical path switching unit 223 moves (slides) the light shielding member 224 in either the optical path through which the WIDE optical lens 222W emits light or the optical path through which the TELE optical lens 222T emits light. As a result, the optical path of the reflected light from the subject incident on the image sensor 212 is switched to the optical path of either the WIDE optical lens 222W or the TELE optical lens 222T, according to the information on the optical lens 222 used first that is set in advance by the user of the endoscope apparatus 1 and stored in the image processing parameter storage section 1132. As a result, the image sensor 212 transmits the pixel signal representing the captured image of the subject in the object to the main body 10. As a result, the image generation processing unit 1133 generates an image (video) of the subject according to the pixel signal amplified by the limiting amplifier circuit 150, and the electronic zoom processing unit 1134 performs electronic zoom processing (zoom magnification=1 times) to generate the final image (video) of the subject and output it to the system control unit 111. Then, the system control unit 111 (more specifically, the display control unit 1113) causes the display device 30 to display the final image (video) of the subject generated by the electronic zoom processing unit 1134.

Thereafter, the image processing control unit 1131 determines whether or not the WIDE optical lens 222W is set as the optical lens 222 that emits light to the image sensor 212 in the initial setting process of step S102 (step S103).

When it is determined as a result of the determination in step S103 that the WIDE optical lens 222W is not set ("NO" in step S103), the image processing control unit 1131 advances the process to step S301.

Figure 3B:
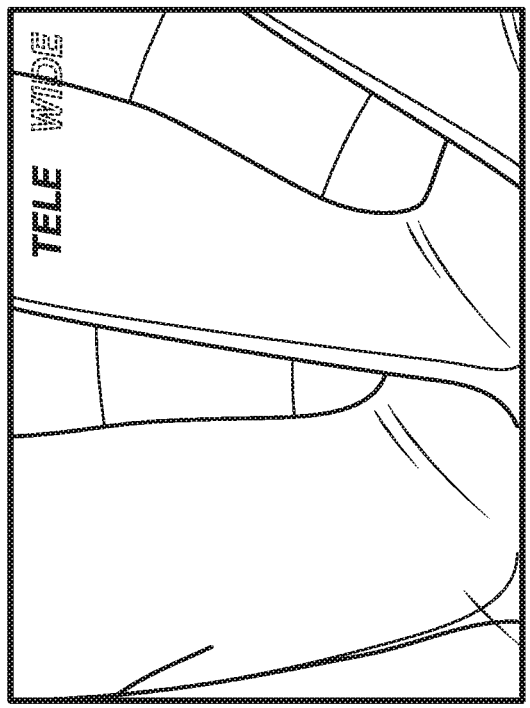
FIGS. 3A and 3B are diagrams showing an example of a method of notifying of the optical path selected in the endoscope apparatus according to the first embodiment of the present invention.
Figure 3A:
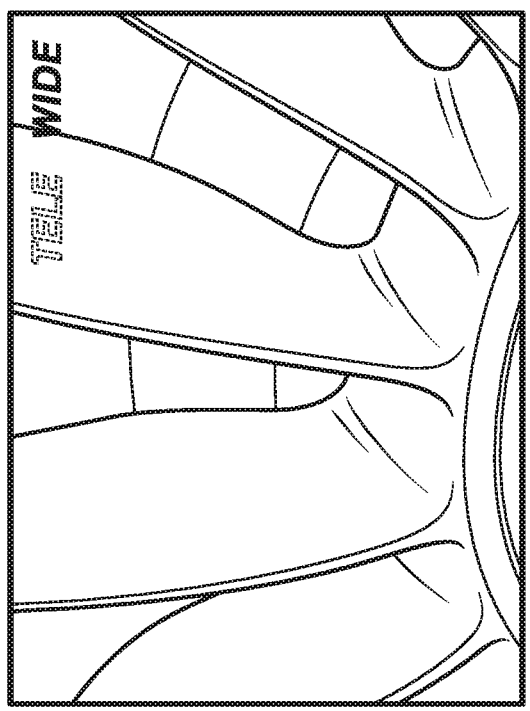

On the other hand, when it is determined as a result of the determination in the step S103 that the WIDE optical lens 222W is set ("YES" in the step S103), the image processing control unit 1131 outputs an optical path switching drive signal for switching the optical path of the optical lens 222 that emits light to the image sensor 212 to the optical path of the WIDE optical lens 222W, to the optical path switching unit 223 via the optical path switching drive circuit 160 and the corresponding signal line. In addition, the image processing control unit 1131 notifies the system control unit 111 that the optical path of the optical lens 222 that emits light to the image sensor 212 is switched to the optical path of the WIDE optical lens 222W (step S201). As a result, for example, as shown in FIG. 3A, the system control unit 111 (more specifically, the display control unit 1113) superimposes information on the optical lens 222 currently emitting light to the image sensor 212 as an on-screen display image on the final image (video) of the subject generated by the electronic zoom processing unit 1134 and causes the display device 30 to display the superimposed information. FIG. 3 (a) shows an example in which, based on the pixel signal of the image of the subject that is acquired by the image sensor 212 capturing the reflected light from the subject emitted to the optical path of the WIDE optical lens 222W, information indicating that the optical path of the WIDE optical lens 222W is currently selected is superimposed on the image (video) of the subject finally generated by the electronic zoom processing unit 1134 as an on-screen display image and displayed on the display device 30. More specifically, an example is shown in which the letters "WIDE" indicating that the optical path of the WIDE optical lens 222W is selected are highlighted with a light color or the like, and the letters "TELE" indicating that the optical path of the TELE optical lens 222T is selected are grayed out, for example, in gray, thereby notifying the user of the endoscope apparatus 1 that the optical path of the WIDE optical lens 222W is currently selected, so that the user can confirm the selection. The method of notifying the user of the endoscope apparatus 1 of the information on the optical lens 222 currently emitting light to the image sensor 212 is not limited to a method of superimposing an on-screen display image as shown in FIG. 3 (a). For example, only the information on the optical lens 222 currently emitting light to the image sensor 212 (here, the letters "WIDE" representing the optical path of the currently selected WIDE optical lens 222W) may be superimposed on the image (video) of the subject as an on-screen display image to be displayed on the display device 30.

When the WIDE optical lens 222W is set as the optical lens 222 for emitting light to the image sensor 212 in the initial setting process of step S102, the optical path switching unit 223 already moves (slides) the light shielding member 224 in a state in which the optical path of the WIDE optical lens 222W is selected. Therefore, even if the image processing control unit 1131 outputs the optical path switching drive signal to the optical path switching unit 223 in the process of step S201, the light shielding member 224 is not actually moved (slid) by the optical path switching unit 223. Therefore, this means that, in the processing of the first step S201 after the initial setting processing in step S102, the image processing control unit 1131 outputs the optical path switching drive signal again for precaution. Therefore, the output of the optical path switching drive signal in the image processing control unit 1131 may be omitted as long as the processing in the first step S201 after the initial setting processing in step S102 is performed.

Subsequently, the image processing control unit 1131 determines whether or not there is a zoom instruction from the user of the endoscope apparatus 1 (step S202). In the processing of step S202, the image processing control unit 1131 determines whether information on the zoom magnification is included in the setting related to the photographing operation set by the UART by the system control unit 111, thereby determining whether or not there is a zoom instruction from the user of the endoscope apparatus 1.

When it is determined as a result of the determination in step S202 that there is no zoom instruction from the user of the endoscope apparatus 1 ("NO" in step S202), the image processing control unit 1131 repeats the determination in step S202.

On the other hand, when it is determined as a result of the determination in step S202 that there is a zoom instruction from the user of the endoscope apparatus 1 ("YES" in step S202), the image processing control unit 1131 determines whether or not the zoom magnification instructed by the user of the endoscope apparatus 1 is equal to or greater than the optical magnification of the TELE optical lens 222T (step S203). For example, when the optical magnification of the TELE optical lens 222T is 2 times, it is determined whether or not the zoom magnification instructed by the user of the endoscope apparatus 1 by the zoom instruction is 2 times or more. Through the process of step S203, the image processing control unit 1131 switches the optical lens 222 provided in the optical adapter 22 to photograph the image (video) of the original subject to which the electronic zoom processing unit 1134 performs the electronic zoom processing, and it is determined whether or not deterioration of the image quality of the final image (video) of the subject enlarged to the instructed zoom magnification can be reduced (suppressed).

When it is determined that the zoom magnification instructed by the user of the endoscope apparatus 1 is not equal to or greater than the optical magnification of the TELE optical lens 222T ("NO" in step S203), the image processing control unit 1131 determines that deterioration in image quality due to the electronic zoom processing performed by the electronic zoom processing unit 1134 on the image (video) of the subject photographed with the WIDE optical lens 222W for wide angles does not exceed a predetermined range. That is, when the zoom magnification instructed by the user of the endoscope apparatus 1 is a magnification that does not exceed (falls below) the optical magnification of the TELE optical lens 222T, the image processing control unit 1131 determines that deterioration of image quality due to electronic zoom processing performed by the electronic zoom processing unit 1134 on an image (video) of the subject photographed using the WIDE optical lens 222W for wide angles does not exceed a predetermined range. Therefore, the image processing control unit 1131 outputs the zoom magnification set by the system control unit 111 to the electronic zoom processing unit 1134 as a zoom magnification of the electronic zoom (hereinafter referred to as "electronic zoom magnification"). Then, the image processing control unit 1131 causes the electronic zoom processing unit 1134 to execute electronic zooming processing with the output zoom magnification (step S204). As a result, the electronic zoom processing unit 1134 performs an electronic zoom process on the image (video) of the subject, which captures the reflected light from the subject emitted from the WIDE optical lens 222W and output from the image generation processing unit 1133, according to the zoom magnification, which is output from the image processing control unit 1131, so as to generate the final image (video) of the subject, and outputs the generated final image (video) of the subject to the system control unit 111. Then, the system control unit 111 (more specifically, the display control unit 1113) causes the display device 30 to display the final image (video) of the subject generated by the electronic zoom processing unit 1134. Thereafter, the image processing control unit 1131 returns the processing to step S202 and repeats the processing of steps S202 to S204.

On the other hand, when it is determined as a result of the determination in step S203 that the zoom magnification instructed by the user of the endoscope apparatus 1 is equal to or greater than the optical magnification of the TELE optical lens 222T ("YES" in step S203), the image processing control unit 1131 determines that deterioration in image quality due to electronic zoom processing performed by the electronic zoom processing unit 1134 on the image (video) of the subject captured by the WIDE optical lens 222W for wide angles exceeds a predetermined range. That is, when the zoom magnification instructed by the user of the endoscope apparatus 1 is the same as the optical magnification of the TELE optical lens 222T or exceeds the optical magnification of the TELE optical lens 222T, the image processing control unit 1131 determines that that deterioration in image quality due to the electronic zoom processing performed by the electronic zoom processing unit 1134 on the image (video) of the subject photographed by the WIDE optical lens 222W for wide angles exceeds a predetermined range. Therefore, the image processing control unit 1131 sets the electronic zoom magnification to be output to the electronic zoom processing unit 1134 to the electronic zoom magnification based on the zoom magnification instructed by the user of the endoscope apparatus 1 (step S205). Then, the image processing control unit 1131 advances the process to step S301.

Note that the electronic zoom magnification output by the image processing control unit 1131 to the electronic zoom processing unit 1134 in the process of step S205 is the zoom magnification instructed by the user of the endoscope apparatus 1, that is, it is determined in consideration of the optical magnification of the TELE optical lens 222T with respect to the zoom magnification set by the system control unit 111. More specifically, it is the zoom magnification acquired by dividing the zoom magnification set from the system control unit 111 by the optical magnification of the TELE optical lens 222T. For example, when the optical magnification of the TELE optical lens 222T is 2 times and the zoom magnification set from the system control unit 111 is 3 times, the image processing control unit 1131 sets the electronic zoom magnification as 3 times/2 times=1.5 times and outputs it to the electronic zoom processing unit 1134. Further, for example, when the optical magnification of the TELE optical lens 222T is 2 times and the zoom magnification set from the system control unit 111 is 4 times, the image processing control unit 1131 sets the electronic zoom magnification as 4 times/2 times=2 and outputs it to the electronic zoom processing unit 1134. Further, for example, when the optical magnification of the TELE optical lens 222T is 3 times and the zoom magnification set from the system control unit 111 is 3 times, the image processing control unit 1131 sets the electronic zoom magnification as 3 times/3 times=1 and outputs it to the electronic zoom processing unit 1134. Further, for example, when the optical magnification of the TELE optical lens 222T is 3 times and the zoom magnification set from the system control unit 111 is 4 times, the image processing control unit 1131 sets the electronic zoom magnification as 4 times/3 times=1.33 times and outputs it to the electronic zoom processing unit 1134.

Subsequently, the image processing control unit 1131 executes the processing of step S301. The process of step S301 is performed when it is determined as a result of the determination in step S103 that the WIDE optical lens 222W is not set as the optical lens 222 that emits light to the image sensor 212 in the initial setting process in step S102 ("NO" in step S103), and when it is determined as a result of the determination in step S204 that the electronic zoom magnification is equal to or greater than the optical magnification of the TELE optical lens 222T ("YES" in step S203).

In the processing of step S301, the image processing control unit 1131 outputs an optical path switching drive signal, which switches the optical path of the optical lens 222 emitting light to the image sensor 212 to the optical path of the TELE optical lens 222T, to the optical path switching unit 223 via the optical path switching drive circuit 160 and the corresponding signal line. Further, the image processing control unit 1131 notifies the system control unit 111 that the optical path of the optical lens 222 that emits light to the image sensor 212 is switched to the optical path of the TELE optical lens 222T. As a result, for example, as shown in FIG. 3 (b), the system control unit 111 (more specifically, the display control unit 1113) displays on the display device 30 the information representing the optical lens 222 currently emitting light to the image sensor 212 as an on-screen display image in the final image of the subject generated by the electronic zoom processing unit 1134. FIG. 3 (b) shows an example in which, based on the pixel signal of the subject image captured by the image sensor 212 by the reflected light from the subject emitted to the optical path of the TELE optical lens 222T, information indicating that the optical path of the TELE optical lens 222T is currently selected is superimposed as an on-screen display image on the final image (video) of the subject generated by the electronic zoom processing unit 1134 and displayed on the display device 30. More specifically, it shows an example in which the letters "WIDE" indicating that the optical path of the WIDE optical lens 222W is selected are grayed out, for example, in gray, and the letters "TELE" indicating that the optical path of the TELE optical lens 222T is selected are highlighted with a light color or the like, so that the user of the endoscope apparatus 1 can be notified and confirm that the optical path of the TELE optical lens 222T is currently selected. The method of notifying the user of the endoscope apparatus 1 of the information of the optical lens 222 currently emitting light to the image sensor 212 it is not limited to the method of superimposing the on-screen display image as shown in FIG. 3 (b). For example, only information on the optical lens 222 currently emitting light to the image sensor 212 (in this case, the letters "TELE" representing the optical path of the currently selected TELE optical lens 222T) may be superimposed on the image (video) of the subject as an on-screen display image and displayed on the display device 30.

In the initial setting process of step S102, when the TELE optical lens 222T is set as the optical lens 222 that emits light to the image sensor 212, the optical path switching unit 223 has already moved (slid) the light shielding member 224 into a state in which the optical path of the TELE optical lens 222T is selected. Therefore, in the process of step S301, even if the image processing control unit 1131 outputs the optical path switching drive signal to the optical path switching unit 223, the light shielding member 224 is not actually moved (slid) by the optical path switching unit 223. Therefore, this means that, also in the processing of the initial step S301 after the initial setting processing in step S102, the image processing control unit 1131 outputs the optical path switching drive signal again for precaution. Therefore, as long as the processing in the first step S301 after the initial setting processing in step S102 is performed, similarly to the processing in step S201, the output of the optical path switching drive signal in the image processing control unit 1131 may be omitted.

Subsequently, the image processing control unit 1131 determines whether or not there is a zoom instruction from the user of the endoscope apparatus 1 (step S302). In the process of step S302, similarly to the process in step S202, the image processing control unit 1131 determines whether or not the information on the zoom magnification is included in the setting related to the photographing operation set by the UART by the system control unit 111, thereby determining whether or not there is a zoom instruction from the user of the endoscope apparatus 1.

When it is determined as a result of the determination in step S302 that there is no zoom instruction from the user of the endoscope apparatus 1 ("NO" in step S302), the image processing control unit 1131 repeats the determination in step S302.

On the other hand, when it is determined as a result of the determination in step S302 that there is a zoom instruction from the user of the endoscope apparatus 1 ("YES" in step S302), the image processing control unit 1131 determines whether or not the zoom magnification instructed by the user of the endoscope apparatus 1 is lower than the optical magnification of the TELE optical lens 222T (step S303). For example, when the optical magnification of the TELE optical lens 222T is 2 times, it is determined whether or not the zoom magnification instructed by the user of the endoscope apparatus 1 by the zoom instruction is a magnification less than 2 times. Through the processing in step S303, the image processing control unit 1131 determines whether or not to photograph the image (video) of the original subject to which the electronic zoom processing unit 1134 performs the electronic zoom by switching (returning to original) the optical lens 222 provided in the optical adapter 22. That is, the image processing control unit 1131 determines whether or not to enlarge the image (video) of the subject photographed by the WIDE optical lens 222W to the instructed zoom magnification to make it the final image (video) of the subject.

When it is determined as a result of the determination in step S303 that the zoom magnification instructed by the user of the endoscope apparatus 1 is not lower than the optical magnification of the TELE optical lens 222T ("NO" in step S303), the image processing control unit 1131 determines to cause the electronic zoom processing unit 1134 to perform the electronic zoom process on the image (video) of the subject photographed by the TELE optical lens 222T for telephoto. That is, when the zoom magnification instructed by the user of the endoscope apparatus 1 is a magnification that does not fall below the optical magnification of the TELE optical lens 222T, it is determined to cause the electronic zoom processing unit 1134 to perform the electronic zoom processing on the image (video) of the subject photographed by the TELE optical lens 222T for telephoto. Therefore, the image processing control unit 1131 outputs the electronic zoom magnification based on the zoom magnification set from the system control unit 111 to the electronic zoom processing unit 1134. Then, the image processing control unit 1131 causes the electronic zoom processing unit 1134 to execute electronic zooming processing with the output zoom magnification (step S304). As a result, the electronic zoom processing unit 1134 applies electronic zoom processing to the image (video) of the subject, which captures the reflected light from the subject emitted from the TELE optical lens 222T output from the image generation processing unit 1133, according to the zoom magnification output from the image processing control unit 1131, and generates the final image (video) of the subject to output the generated final image (video) of the subject to the system control unit 111. Then, the system control unit 111 (more specifically, the display control unit 1113) causes the display device 30 to display the final image (video) of the subject generated by the electronic zoom processing unit 1134.

Thereafter, the image processing control unit 1131 returns the processing to step S302 and repeats the processing of steps S302 to S304.

Note that, in the process of step S304, the electronic zoom magnification that the image processing control unit 1131 outputs to the electronic zoom processing unit 1134 is a zoom magnification determined based on a concept similar to the electronic zoom magnification output to the electronic zoom processing unit 1134 by the image processing control unit 1131 in the process of step S205. That is, it is a zoom magnification acquired by dividing the zoom magnification set from the system control unit 111 (the zoom magnification instructed by the user of the endoscope apparatus 1) by the optical magnification of the TELE optical lens 222T. For example, when the optical magnification of the TELE optical lens 222T is 2 times and the zoom magnification set from the system control unit 111 is 3 times, the image processing control unit 1131 sets the electronic zoom magnification as 3 times/2 times=1.5 times and outputs it to the electronic zoom processing unit 1134. Further, for example, when the optical magnification of the TELE optical lens 222T is 2 times and the zoom magnification set from the system control unit 111 is 4 times, the image processing control unit 1131 sets the electronic zoom magnification as 4 times/2 times=2 times and outputs it to the electronic zoom processing unit 1134. Further, for example, when the optical magnification of the TELE optical lens 222T is 2 times and the zoom magnification set from the system control unit 111 is 5 times, the image processing control unit 1131 sets the electronic zoom magnification as 5 times/2 times=2.5 times and outputs it to electronic zoom processing unit 1134. Further, for example, when the optical magnification of the TELE optical lens 222T is 3 times and the zoom magnification set from the system control unit 111 is 4 times, the image processing control unit 1131 sets the electronic zoom magnification as 4 times/3 times=1.33 times and outputs it to the electronic zoom processing unit 1134. Further, for example, when the optical magnification of the TELE optical lens 222T is 3 times and the zoom magnification set from the system control unit 111 is 5 times, the image processing control unit 1131 sets the electronic zoom magnification as 5 times/3 times=1.67 times and outputs it to the electronic zoom processing unit 1134. As a result, it is possible for the electronic zoom processing unit 1134 to subject the image (video) of the subject output from the image generation processing unit 1133 to electronic zoom processing with a continuous (seamless) zoom magnification, and generate the final image (video) of the subject. Thus, the image (video) of the subject displayed on the display device 30 is continuously zoomed (enlarged or reduced) without discomfort.

On the other hand, when it is determined as a result of the determination in step S303 that the zoom magnification instructed by the user of the endoscope apparatus 1 is a magnification lower than the optical magnification of the TELE optical lens 222T ("YES" in step S303), the process control unit 1131 determines to cause the electronic zoom processing unit 1134 to perform the electronic zoom process on the image (video) of the subject photographed by the WIDE optical lens 222W for wide angles. That is, when the zoom magnification instructed by the user of the endoscope apparatus 1 is lower than the optical magnification of the TELE optical lens 222T, the image processing control unit 1131 determines to cause the electronic zoom processing unit 1134 to perform the electronic zoom processing on the image (video) of the subject photographed by the WIDE optical lens 222W for wide angles. Therefore, the image processing control unit 1131 sets the electronic zoom magnification to be output to the electronic zoom processing unit 1134 to the zoom magnification instructed by the user of the endoscope apparatus 1 (the zoom magnification set by the system control unit 111) (Step S305). Then, the image processing control unit 1131 advances the processing to step S201. As a result, the processing of the image processing control unit 1131 is processing of steps S201 to S205 of applying the electronic zoom processing to the image (video) of the subject photographed by the WIDE optical lens 222W.

As described above, when the electronic zoom processing unit 1134 is caused to perform the electronic zoom processing, the image processing control unit 1131 automatically switches the optical lens 222 provided in the optical adapter 22 according to the zoom magnification instructed by the user of the endoscope apparatus 1. Thereby, in the endoscope apparatus 1, the final image (video) of the subject enlarged by the electronic zoom processing unit 1134 performing the electronic zoom process according to the instructed zoom magnification can be displayed on the display device 30 in a state where deterioration of the image quality of the enlarged final image (video) of the subject is reduced (suppressed).

In the above description, the timing at which the image processing control unit 1131 causes the optical path switching unit 223 to switch the optical path for emitting light to the image sensor 212 is not described. That is, in the endoscope apparatus 1, the timing at which the image processing control unit 1131 outputs the optical path switching drive signal is not particularly specified. Here, the timing at which the image processing control unit 1131 outputs the optical path switching drive signal may be a timing synchronized with the imaging timing of the subject image by the image sensor 212. More specifically, the image processing control unit 1131 may output to the optical path switching unit 223 an optical path switching drive signal for switching the optical path for emitting light to the image sensor 212 in the period during which the image sensor 212 outputs the pixel signal capturing the subject image, that is, within the period from the end of the exposure period to the start of the next exposure period in the image sensor 212. In this case, the optical path switching unit 223 moves (slides) the light shielding member 224 at a timing synchronized with the image sensor 212 to either one of the optical path through which the WIDE optical lens 222W emits light or the optical path through which the TELE optical lens 222T emits light, according to the optical path switching drive signal output from the image processing control unit 1131. Thereby, in the image sensor 212, within a period from the end of the exposure period to the start of the next exposure period, the reflected light from the subject emitted to the entire imaging region is switched to the reflected light from the subject that is emitted to the optical path of either one of the WIDE optical lens 222W or the TELE optical lenses 222T. On the other hand, the timing at which the image processing control unit 1131 outputs the optical path switching drive signal may not be synchronized with the imaging timing of the subject image by the image sensor 212, that is, may be asynchronous timing. In this case, the image (video) of the subject displayed on the display device 30 in the endoscope apparatus 1 is disturbed when the optical path of the optical lens 222 is switched. However, for example, when the system control unit 111 is notified from the image processing control unit 1131 of the fact that the optical path switching drive signal is output to the optical path switching unit 223, by controlling the display control unit 1113 not to update the image (video) of the subject displayed on the display device 30 for a certain period (for example, 1 second), it is possible to not display the disturbance of the image (video) of the subject when the optical path of the optical lens 222 is switched on the display device 30. In other words, when the optical path of the optical lens 222 is switched, by temporarily fixing the image (video) of the subject displayed on the display device 30, that is, by freezing it, it is also possible to not display the disturbance of the image of the subject (video) on the display device 30. Moreover, in this case, since the image (video) of the subject is not refreshed for a certain period of time (the same image (video) is continuously displayed), a sense of incompatibility appears in the display of the image (video) of the subject on the display device 30, and therefore it is possible for the user of the endoscope apparatus 1 to notice that the switching of the optical path of the optical lens 222 has been executed.

According to the first embodiment, an endoscope apparatus (endoscope apparatus 1) is configured to include: the insertion portion (the insertion portion 20) formed so as to extend in the longitudinal direction along the predetermined central axis and having the distal end portion; an optical path switching unit (an optical path switching unit 223 and a light shielding member 224) disposed inside the insertion portion (insertion portion 20) and switching the optical path so that only one of the first subject image and the second subject image is formed on the imaging area (capturing area) on which a first subject image (subject image) of the subject formed by light (reflected light from the subject) emitted from the first objective optical system (WIDE optical lens 222W) arranged at the distal end portion and a second subject image (subject image) of the subject formed by light (reflected light from the subject) emitted from the second objective optical system (TELE optical lens 222T) arranged at the distal end portion and whose optical magnification is higher than that of the optical lens 222W are commonly imaged; an imaging element (an image sensor 212) that generates an image acquired by picking up the first subject image and the second subject image formed on the imaging area (a pixel signal (for example, a RAW signal) representing the subject image); and an endoscope processing unit (endoscope processing unit 110) that controls the switching of the optical path based on the input zoom magnification (instructed by the user) and performs image processing on the image.

Further, according to the first embodiment, an endoscope apparatus 1 in which, when the zoom magnification is equal to or larger than the optical magnification of the TELE optical lens 222T, the endoscope processing unit 110 switches the optical path to the optical path where the second subject image is formed (the optical path for photographing the subject by the TELE optical lens 222T), and when the zoom magnification is a magnification lower than the optical magnification of the TELE optical lens 222T, the endoscope processing unit 110 switches the optical path to the optical path where the first subject image is formed (the optical path for photographing the subject by the WIDE optical lens 222W) is configured.

Further, according to the first embodiment, an endoscope apparatus 1 in which the endoscope processing unit 110 changes the parameters of image processing according to the optical path that is being switched is configured.

According to the first embodiment, an endoscope apparatus 1 in which the endoscope processing unit 110 performs electronic zooming image processing (electronic zoom processing by the electronic zoom processing unit 1134) for enlarging the image is configured.

Further, according to the first embodiment, an endoscope apparatus 1 in which the image is enlarged with the electronic zoom magnification based on the zoom magnification in the electronic zoom image processing is configured.

Further, according to the first embodiment, an endoscope apparatus 1 in which the endoscope processing unit 110 changes the electronic zoom magnification according to the switched optical path is configured.

Further, according to the first embodiment, an endoscope apparatus 1 in which, when the optical path is switched to the optical path on which the second subject image is formed, the endoscope processing unit 110 divides the zoom magnification by the optical magnification of the TELE optical lens 222T and sets the divided magnification as the electronic zoom magnification, and when the optical path is switched to the optical path on which the first subject image is formed, the endoscope processing unit 110 sets the zoom magnification as the electronic zoom magnification is configured.

Further, according to the first embodiment, an endoscope apparatus 1 in which the endoscope processing unit 110 sets the center position (optical center) of the image acquired by imaging the second subject image as the center position (zooming center) of the image to be enlarged in the electronic zoom image processing is configured.

Further, according to the first embodiment, an endoscope apparatus 1 in which the endoscope processing unit 110 outputs the optical path switching drive signal to the optical path switching unit (the optical path switching unit 223) when switching the optical path, and the optical path switching unit 223 switches the optical path by sliding a light shielding member (shielding member 224) shielding one of the optical paths by a magnetic field generated according to the polarity of the current in the optical path switching drive signal is configured.

Further, according to the first embodiment, an endoscope apparatus 1 in which the insertion portion 20 includes a scope portion (scope portion 21) including a flexible cord portion, and an optical adapter (optical adapter 22) detachable from the distal end side of the scope portion 21, the WIDE optical lens 222W, the TELE optical lens 222T, and the optical path switching unit (the optical path switching unit 223 and the light shielding member 224) are disposed in the optical adapter 22, and the image sensor 212 is arranged on the distal end side of the scope portion 21 is configured.

Further, according to the first embodiment, an endoscope apparatus 1 in which the endoscope processing unit 110 notifies of the optical path that is being switched is configured.

Further, according to the first embodiment, provided is a control method of the endoscope apparatus (endoscope apparatus 1) including: the insertion portion (the insertion portion 20) formed so as to extend in the longitudinal direction along the predetermined central axis and having the distal end portion; an optical path switching unit (an optical path switching unit 223 and a light shielding member 224) disposed inside the insertion portion (insertion portion 20) and switching the optical path so that only one of the first subject image and the second subject image is formed on the imaging area (capturing area) on which a first subject image (subject image) of the subject formed by light (reflected light from the subject) emitted from the first objective optical system (WIDE optical lens 222W) arranged at the distal end portion and a second subject image (subject image) of the subject formed by light (reflected light from the subject) emitted from the second objective optical system (TELE optical lens 222T) arranged at the distal end portion and whose optical magnification is higher than that of the optical lens 222W are commonly imaged; an imaging element (an image sensor 212) that generates an image acquired by picking up the first subject image and the second subject image formed on the imaging area (a pixel signal (for example, a RAW signal) representing the subject image); and an endoscope processing unit (endoscope processing unit 110) that controls the switching of the optical path based on the input zoom magnification (instructed by the user) and performs image processing on the image. The control method of the endoscope apparatus (endoscope apparatus 1) includes: switching, by the endoscope processing section 110, the optical path to the optical path where the second object image is formed (an optical path for photographing the subject by the TELE optical lens 222T) when the zoom magnification is equal to or larger than the optical magnification of the TELE optical lens 222T; and switching, by the endoscope processing unit 110, the optical path to the optical path where the first object image is formed (an optical path for photographing the subject by the WIDE optical lens 222W) when the zoom magnification is lower than the optical magnification of the TELE optical lens 222T.

Further, according to the first embodiment, provided is a control program of an endoscope apparatus 1 including: the insertion portion (the insertion portion 20) formed so as to extend in the longitudinal direction along the predetermined central axis and having the distal end portion; an optical path switching unit (an optical path switching unit 223 and a light shielding member 224) disposed inside the insertion portion (insertion portion 20) and switching the optical path so that only one of the first subject image and the second subject image is formed on the imaging area (capturing area) on which a first subject image (subject image) of the subject formed by light (reflected light from the subject) emitted from the first objective optical system (WIDE optical lens 222W) arranged at the distal end portion and a second subject image (subject image) of the subject formed by light (reflected light from the subject) emitted from the second objective optical system (TELE optical lens 222T) arranged at the distal end portion and whose optical magnification is higher than that of the optical lens 222W are commonly imaged; an imaging element (an image sensor 212) that generates an image acquired by picking up the first subject image and the second subject image formed on the imaging area (a pixel signal (for example, a RAW signal) representing the subject image)); and an endoscope processing unit (endoscope processing unit 110) that controls the switching of the optical path based on the input zoom magnification (instructed by the user) and performs image processing on the image. The control program of the endoscope apparatus 1 causes the computer of the endoscope processing section 110 of the endoscope apparatus (endoscope apparatus 1) to execute: a process of switching, by the endoscope processing section 110, the optical path to the optical path where the second object image is formed (an optical path for photographing the subject by the TELE optical lens 222T) when the zoom magnification is equal to or larger than the optical magnification of the TELE optical lens 222T; and a process of switching, by the endoscope processing unit 110, the optical path to the optical path where the first object image is formed (an optical path for photographing the subject by the WIDE optical lens 222W) when the zoom magnification is lower than the optical magnification of the TELE optical lens 222T.

Further, according to the first embodiment, provided is a computer-readable recording medium on which a control program is recorded for an endoscope apparatus 1 including: the insertion portion (the insertion portion 20) formed so as to extend in the longitudinal direction along the predetermined central axis and having the distal end portion; an optical path switching unit (an optical path switching unit 223 and a light shielding member 224) disposed inside the insertion portion (insertion portion 20) and switching the optical path so that only one of the first subject image and the second subject image is formed on the imaging area (capturing area) on which a first subject image (subject image) of the subject formed by light (reflected light from the subject) emitted from the first objective optical system (WIDE optical lens 222W) arranged at the distal end portion and a second subject image (subject image) of the subject formed by light (reflected light from the subject) emitted from the second objective optical system (TELE optical lens 222T) arranged at the distal end portion and whose optical magnification is higher than that of the optical lens 222W are commonly imaged; an imaging element (an image sensor 212) that generates an image acquired by picking up the first subject image and the second subject image formed on the imaging area (a pixel signal (for example, a RAW signal) representing the subject image); and an endoscope processing unit (endoscope processing unit 110) that controls the switching of the optical path based on the input zoom magnification (instructed by the user) and performs image processing on the image. The control program of the endoscope apparatus 1 causes the computer of the endoscope processing section 110 of the endoscope apparatus (endoscope apparatus 1) to execute: a process of switching, by the endoscope processing section 110, the optical path to the optical path where the second object image is formed (an optical path for photographing the subject by the TELE optical lens 222T) when the zoom magnification is equal to or larger than the optical magnification of the TELE optical lens 222T; and a process of switching, by the endoscope processing unit 110, the optical path to the optical path where the first object image is formed (an optical path for photographing the subject by the WIDE optical lens 222W) when the zoom magnification is lower than the optical magnification of the TELE optical lens 222T.

As described above, in the endoscope apparatus 1 according to the first embodiment of the present invention, the optical adapter 22 mounted on the distal end portion of the insertion portion 20, that is, the distal end side of the scope portion 21, has a plurality of optical lenses 222 (objective lenses) having different optical magnifications (two in the endoscope apparatus 1 of the first embodiment, a WIDE optical lens 222W for wide angles and a TELE optical lens 222T for telephoto). In the endoscope apparatus 1 according to the first embodiment of the present invention, the endoscope processing unit 110 (more specifically, the electronic zoom processing unit 1134) provided in the main body 10 performs electronic zoom processing on the image (video) of the subject, which is acquired by capturing the subject image in the subject emitted to the optical path of the currently selected WIDE optical lens 222W, in accordance with the zoom magnification instructed by the user of the endoscope apparatus 1, and generates the final image (video) of the subject to be displayed on the display device 30. At this time, in the endoscope apparatus 1 according to the first embodiment of the present invention, the endoscope processing unit 110 (more specifically, the image processing control unit 1131) provided in the main body 10 determines the zoom magnification instructed by the user of the endoscope apparatus 1. In the endoscope apparatus 1 according to the first embodiment of the present invention, when the image processing control unit 1131 determines that the instructed zoom magnification is greater than the optical magnification of the TELE optical lens 222T, the optical path of the WIDE optical lens 222W selected as the optical path for emitting the light to the image sensor 212 is automatically switched to the optical path of the TELE optical lens 222T. Thereafter, in the endoscope apparatus 1 according to the first embodiment of the present invention, the endoscope processing unit 110 (more specifically, the electronic zoom processing unit 1134) provided in the main body 10 performs an electronic zooming process on the image (video) of the subject, which is acquired by capturing the subject image in the subject emitted to the optical path of the currently selected TELE optical lens 222T, in accordance with the zoom magnification instructed by the user of the endoscope apparatus 1, and generates the final image (video) of the subject to be displayed on the display device 30. Consequently, in the endoscope apparatus 1 according to the first embodiment of the present invention, by performing the electronic zoom processing with a low zoom magnification on the image (video) of the subject, which is acquired by capturing the optically enlarged subject image, the zoom magnification can be enlarged to a necessary zoom magnification. Thus, in the endoscope apparatus 1 according to the first embodiment of the present invention, it is possible to reduce (suppress) degradation of the image quality of the image (video) of the subject, which is used by being enlarged to be displayed or being enlarged for use of measurement, as compared with a case where an electronic zoom process with a high zoom magnification is performed on an image (video) of the subject, which is acquired by capturing a subject image that is not magnified optically and is enlarged to the necessary zoom magnification.

On the other hand, in the endoscope apparatus 1 according to the first embodiment of the present invention, by performing an electronic zoom process on the image (video) of the subject, which is acquired by capturing the subject image in the subject emitted to the optical path of the currently selected TELE optical lens 222T, even when the final image (video) of the subject to be displayed on the display device 30 is generated, the endoscope processing section 110 (more specifically, the image processing control section 1131) provided in the main body section 10 determines the zoom magnification instructed by the user of the endoscope apparatus 1. In the endoscope apparatus 1 according to the first embodiment of the present invention, when the image processing control unit 1131 determines that the instructed zoom magnification is less than the optical magnification of the TELE optical lens 222T, the optical path of the TELE optical lens 222T selected as the optical path for emitting light to the image sensor 212 is automatically switched to the optical path of the WIDE optical lens 222W. Thereafter, in the endoscope apparatus 1 according to the first embodiment of the present invention, the endoscope processing unit 110 (more specifically, the electronic zoom processing unit 1134) provided in the main body 10 performs an electronic zooming process on the image (video) of the subject, which is acquired by capturing the subject image in the subject emitted to the optical path of the currently selected WIDE optical lens 222W, in accordance with the zoom magnification instructed by the user of the endoscope apparatus 1, and generates the final image (video) of the subject to be displayed on the display device 30. In the endoscope apparatus 1 according to the first embodiment of the present invention, the electronic zoom magnification with respect to the image (video) of the subject, which is acquired by capturing the subject image in the optical path of the WIDE optical lens 222W, is set under the optical magnification of the TELE optical lens 222T, thereby reducing (suppressing) the deterioration of image quality also in the image (video) of the subject captured in the optical path of the WIDE optical lens 222W. With these features, in the endoscope apparatus 1 according to the first embodiment of the present invention, it is possible to improve the inspection accuracy of the subject using the endoscope apparatus 1.

Moreover, in the endoscope apparatus 1 according to the first embodiment of the present invention, the zoom magnification instructed by the user of the endoscope apparatus 1 is determined and selected as the optical path for emitting light to the current image sensor 212, and the optical path of the optical lens 222 (objective lens) is automatically switched. Thus, in the endoscope apparatus 1 according to the first embodiment of the present invention, it is not necessary for the user of the endoscope apparatus 1 to manipulate the endoscope apparatus 1 (more specifically, the user interface 170) in order to switch the optical path of the optical lens 222 (objective lens), that is, the operability of the endoscope apparatus 1 can be improved and complication of examination using the endoscope apparatus 1 can be reduced. Furthermore, in the endoscope apparatus 1 according to the first embodiment of the present invention, it is possible to suppress deterioration of the inspection accuracy of the subject using the endoscope apparatus 1 due to factors such as the user of the endoscope apparatus 1 increasing only the electronic zoom magnification.

In addition, in the endoscope apparatus 1 according to the first embodiment of the present invention, when the zoom magnification instructed by the user of the endoscope apparatus 1 is determined and the optical path for emitting light to the image sensor 212 is switched, the fact that the optical path of the optical lens 222 has been switched is notified of by an on-screen display image superimposed on the image (video) of the subject. Thus, in the endoscope apparatus 1 according to the first embodiment of the present invention, the user of the endoscope apparatus 1 can confirm with ease the optical lens 222 (objective lens) currently selected as the optical path for emitting light to the image sensor 212.

Second Embodiment

Figure 4:
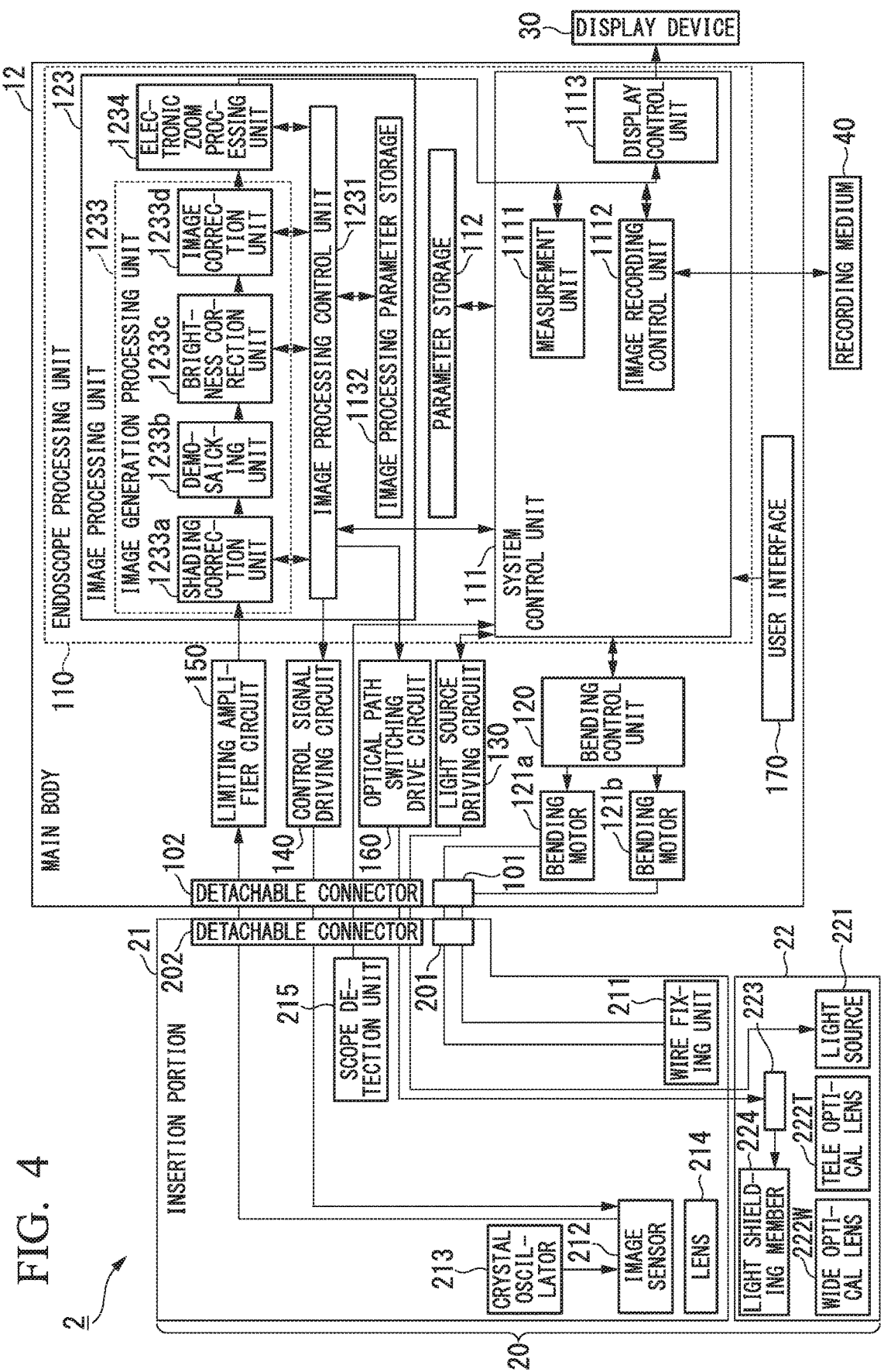
FIG. 4 is a block diagram showing an example of a configuration of an endoscope apparatus according to a second embodiment of the present invention.

Next, an endoscope apparatus according to a second embodiment of the present invention will be described. Note that a case where the endoscope apparatus of the second embodiment is also an industrial endoscope apparatus will be described. FIG. 4 is a block diagram showing an example of the configuration of the endoscope apparatus according to the second embodiment of the present invention. The endoscope apparatus 2 shown in FIG. 4 includes a main body 12 and an elongated insertion portion 20. Also in the endoscope apparatus 2, like the endoscope apparatus 1 of the first embodiment, the display device 30 and the recording medium 40 are connected to the main body 12.

The main body 12 includes an endoscope processing unit 110, a bending control unit 120, two bending motors 121a and 121b, a light source driving circuit 130, a control signal driving circuit 140, a limiting amplifier circuit 150, an optical path switching drive circuit 160, a user interface 170, a wire connection mechanism 101, and a detachable connector 102. Further, the endoscope processing unit 110 includes a system control unit 111, a parameter storage 112, and an image processing unit 123. Further, the system control unit 111 includes a measurement unit 1111, an image recording processing unit 1112, and a display control unit 1113. The image processing unit 123 includes an image processing control unit 1231, an image processing parameter storage 1132, an image generation processing unit 1233, and an electronic zoom processing unit 1234. Further, the image generation processing unit 1233 includes a shading correction unit 1233a, a demosaicking unit 1233b, a brightness correction unit 1233c, and an image correction unit 1233d.

The insertion portion 20 is configured to include a scope portion 21 including a flexible cord section and an optical adapter 22 detachably attached to the distal end side of the scope portion 21. The scope portion 21 includes a wire fixing unit 211, an image sensor 212, a crystal oscillator 213, a lens 214, a scope detection unit 215, a wire connection mechanism 201, and a detachable connector 202. Further, the optical adapter 22 includes a light source 221, a WIDE optical lens 222W, a TELE optical lens 222T, an optical path switching unit 223, and a light shielding member 224. In the scope portion 21, the wire fixing section 211, the image sensor 212, the crystal oscillator 213, and the lens 214 are disposed on the distal end side where the optical adapter 22 is mounted. Also in the following description, the distal end side of the scope portion 21 where the image sensor 212 and the like are disposed and the optical adapter 22 attached to the distal end side of the scope portion 21 are referred to as "distal end portion" of the insertion portion 20.

In the endoscope apparatus 2, the main body 10 of the endoscope apparatus 1 of the first embodiment is replaced with the main body 12. In the endoscope apparatus 2, the image processing unit 113 provided in the endoscope processing unit 110 in the main body 10 in the endoscope apparatus 1 according to the first embodiment is replaced with the image processing unit 123. Furthermore, in the endoscope apparatus 2, the image generation processing unit 1133 provided in the image processing unit 113 in the endoscope apparatus 1 according to the first embodiment is replaced with the image generation processing unit 1233, and the electronic zoom processing unit 1134 is replaced with the electronic zoom processing unit 1234. In the endoscope apparatus 2, the components included in the image generation processing unit 1233 are shown.

The other constituent elements included in the endoscope apparatus 2 are the same constituent elements as those of the endoscope apparatus 1 of the first embodiment. Therefore, in the following explanation, in the components of the endoscope apparatus 2, the same reference numerals are given to the same constituent elements as those of the endoscope apparatus 1 of the first embodiment, and the detailed description relating to each constituent element will be omitted. In the following description, only constituent elements of the endoscope apparatus 2 different from those of the endoscope apparatus 1 of the first embodiment will be described.

In the endoscope apparatus 2, similarly to the endoscope apparatus 1 of the first embodiment, the distal end portion of the flexible insertion portion 20 having a shape extending in the longitudinal direction along a predetermined central axis is set in the subject, and a pixel signal representing the subject image in the subject acquired by photographing by the imaging element disposed at the distal end portion is transmitted to the main body 12 connected to the proximal end side of the insertion portion 20, thereby displaying the image (video) of the captured subject on the display device 30 and recording data of the image of the subject on the recording medium 40. In the endoscope apparatus 2, similarly to the endoscope apparatus 1 according to the first embodiment, the movement and direction of the distal end portion and the photographing operation of the subject by the arranged imaging element and the like when the insertion portion 20 is inserted into the subject are controlled by the main body 12.

However, in the endoscope apparatus 2, components and processes for reducing the difference in angle of view and brightness of the subject image in the subject that the image sensor 212 picks up are added, which appear according to the arrangement and characteristics of the WIDE optical lens 222W and the TELE optical lens 222T provided in the optical adapter 22 attached to the distal end side of the scope portion 21. More specifically, in the optical adapter 22, the WIDE optical lens 222W and the TELE optical lens 222T are arranged side by side, for example. The WIDE optical lens 222W is an optical lens for wide angles, and the TELE optical lens 222T is an optical lens for telephoto. Therefore, in the optical adapter 22, due to the difference in the relationship between the position at which each of the optical lenses 222 is disposed and the position at which the light source 221 provided at the optical adapter 22 is disposed, the incident angles of the reflected light from the subject entering the respective optical lenses 222 are different. Further, in the optical adapter 22, due to the range in which the respective optical lenses 222 collect the reflected light from the subject, that is, the so-called difference in angle of view, the amount of reflected light from the subject, that is, the brightness, differs between the optical lens 222 and the image sensor 212. Although it is an optical characteristic in a general optical lens, in the optical adapter 22, the light amount of the reflected light from the subject emitted from each optical lens 222 toward the image sensor 212 side is different between the central portion and the peripheral portion of the optical lens, that is, the so-called shading characteristics are also different. In such a case, when the electronic zoom process is performed simply based on the center position of the imaging area of the image sensor 212 as a standard position, if the optical path for emitting light to the image sensor 212 is switched from the optical path of the WIDE optical lens 222W to the optical path of the TELE optical lens 222T or vice versa, a shift occurs in the center position and the brightness of the image (video) of the subject displayed on the display device 30.

Therefore, in the endoscope apparatus 2, provided is a component that can reduce this change in the image (video) of the subject appearing when the optical path for emitting light to the image sensor 212 is switched, that is, a component for absorbing a difference in characteristics between the WIDE optical lens 222W and the TELE optical lens 222T. More specifically, in the endoscope apparatus 2, in the same manner as the image processing unit 113 provided in the main body 10 in the endoscope apparatus 1 of the first embodiment, the image processing unit 123 provided in the main body 12 performs control relating to the photographing operation of the subject in the endoscope apparatus 2 and generation of an image (video) of the photographed subject, as well as processing to absorb the difference of characteristics of the WIDE optical lens 222W and the TELE optical lens 222T provided in the optical adapter 22.

Like the image processing unit 113 of the endoscope apparatus 1 according to the first embodiment, the image processing unit 123 outputs a control signal for controlling the image sensor 212 to the image sensor 212, based on various settings related to the activation of the image sensor 212 set by the system control unit 111 and the operation of photographing. Similarly to the image processing unit 113 of the endoscope apparatus 1 according to the first embodiment, the image processing unit 123 generates the image (video) of the subject in the object, based on the pixel signal (for example, RAW signal) of the subject image captured by the image sensor 212 according to the output control signal to be output.

Similarly to the image processing control unit 1131 provided in the image processing unit 113 of the endoscope apparatus 1 according to the first embodiment, the image processing control unit 1231 controls the operation of photographing by the image sensor 212 and the operation of generating the image (video) of the subject by the image generation processing unit 1233, in accordance with the setting related to the photographing operation set by the UART by the system control unit 111. Further, similarly to the image processing control unit 1131 provided in the image processing unit 113 of the endoscope apparatus 1 according to the first embodiment, the image processing control unit 1231 controls the operation of the electronic zoom by the electronic zoom processing unit 1234, in accordance with the information of the zoom magnification included in the setting related to the photographing operation set by the UART by the system control unit 111.

Similarly to the image generation processing unit 1133 provided in the image processing unit 113 of the endoscope apparatus 1 according to the first embodiment, the image generation processing unit 1233 is a digital signal processing unit that that performs various predetermined types of image processing on the pixel signal (for example, RAW signal), which is output from the limiting amplifier circuit 150, of the subject image output by the image sensor 212 provided in the distal end portion, and generates the image (video) of the captured subject in the object. Similarly to the image generation processing unit 1133 provided in the image processing unit 113 of the endoscope apparatus 1 according to the first embodiment, the image generation processing unit 1233 outputs the generated image (video) of the subject to the electronic zoom processing unit 1234.

The shading correction unit 1233a is a digital signal processing unit that performs shading correction processing for correcting shading differing depending on the optical characteristics of the WIDE optical lens 222W and the TELE optical lens 222T. In accordance with the control by the image processing control unit 1231, the shading correction unit 1233a performs shading correction processing corresponding to each of the optical lenses 222, so that the shading appearing in the image (video) of the subject capturing the reflected light from the subject emitted from each of the optical lenses 222 is reduced. More specifically, the shading correction unit 1233a sets a predetermined gain value for each optical lens 222 so that the shading appearing in the image (video) of the subject of the optical lens 222 becomes the same, and multiplies the value (digital value) of each pixel included in the pixel signal (for example, RAW signal) of the subject image output by the image sensor 212 with the gain value to adjust the level of the brightness (luminance) represented by the digital value of each pixel.

In the image processing control unit 1231, the shading correction unit 1233a switches a predetermined gain value for each optical lens 222 multiplied by the value (digital value) of each pixel. More specifically, when switching to the optical path of the optical lens 222 that emits light to the image sensor 212, the image processing control unit 1231 switches the gain value used when the shading correction unit 1233a performs the shading correction processing, in accordance with the zoom magnification instructed by the user of the endoscope apparatus 2. As a result, the shading correction unit 1233a outputs the pixel signal of the subject image whose brightness (luminance) level is adjusted using the switched gain value to the demosaicking unit 1233b as a pixel signal of the subject image photographed and output by the image sensor 212. The pixel signal of the subject image whose brightness (luminance) level is adjusted by the shading correction unit 1233*a* is also a signal (for example, RAW signal) of the same format as the pixel signal of the subject image photographed and output by the image sensor 212.

Here, an example of the gain value used when the shading correction unit 1233*a* performs the shading correction processing will be described. In the following description, it is assumed that the optical adapter 22 has a configuration in which the WIDE optical lens 222W and the TELE optical lens 222T are arranged side by side (in the horizontal direction). In the following description, it is assumed that the characteristics of the respective pixels arranged in the imaging region of the image sensor 212 are uniform, that is, when the subject having the same brightness is photographed, a value (digital value) of each pixel included in the pixel signal (for example, RAW signal) of the subject image output from the image sensor 212 is the same digital value. As described above, the shading correction unit 1233*a* performs shading correction processing on the pixel signal (for example, RAW signal) of the subject image output by the image sensor 212. However, in the following description, it is assumed for ease of explanation that shading appearing in the image (video) of the subject to be generated is corrected.

Figure 5A:
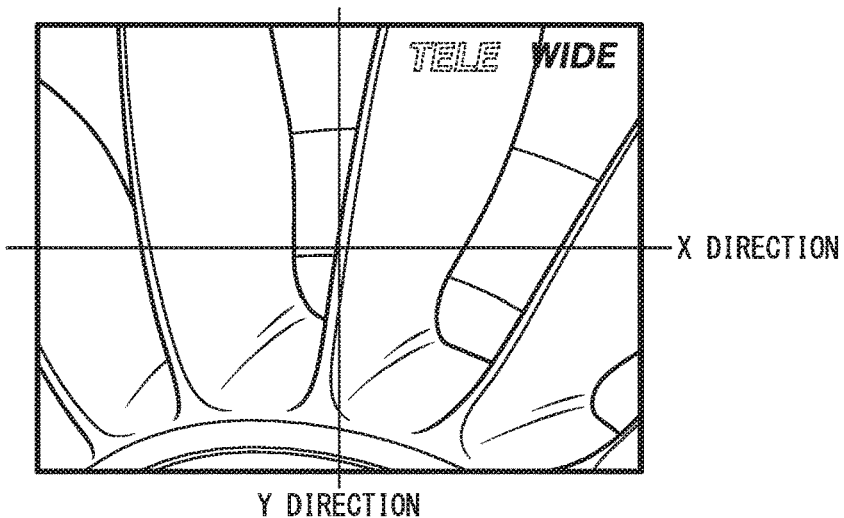
FIGS. 5A to 5C are diagrams for explaining an example of shading correction processing in an endoscope apparatus according to a second embodiment of the present invention.
Figure 5B:
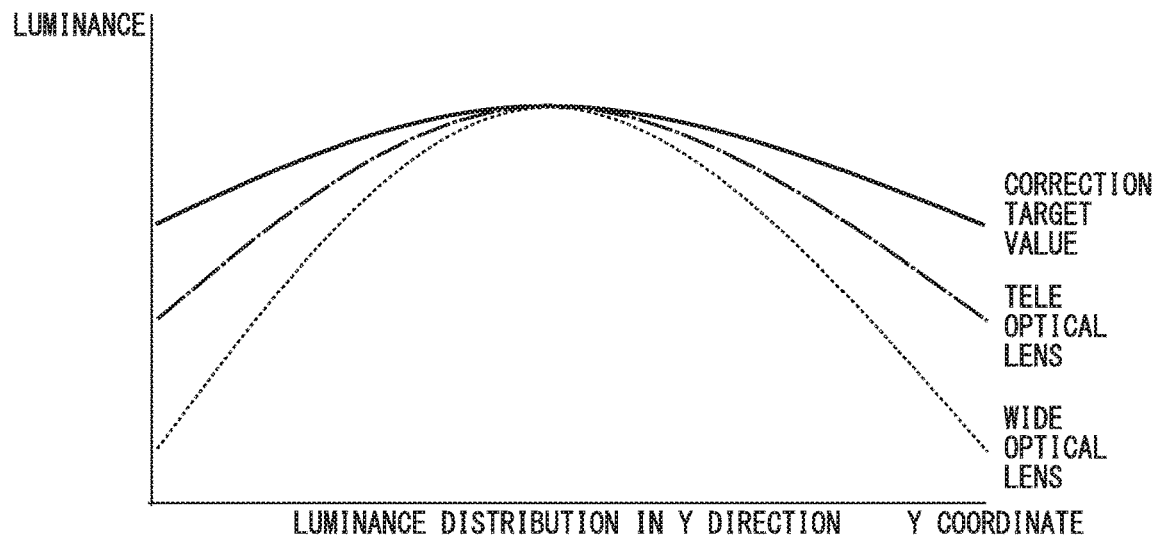
Figure 5C:
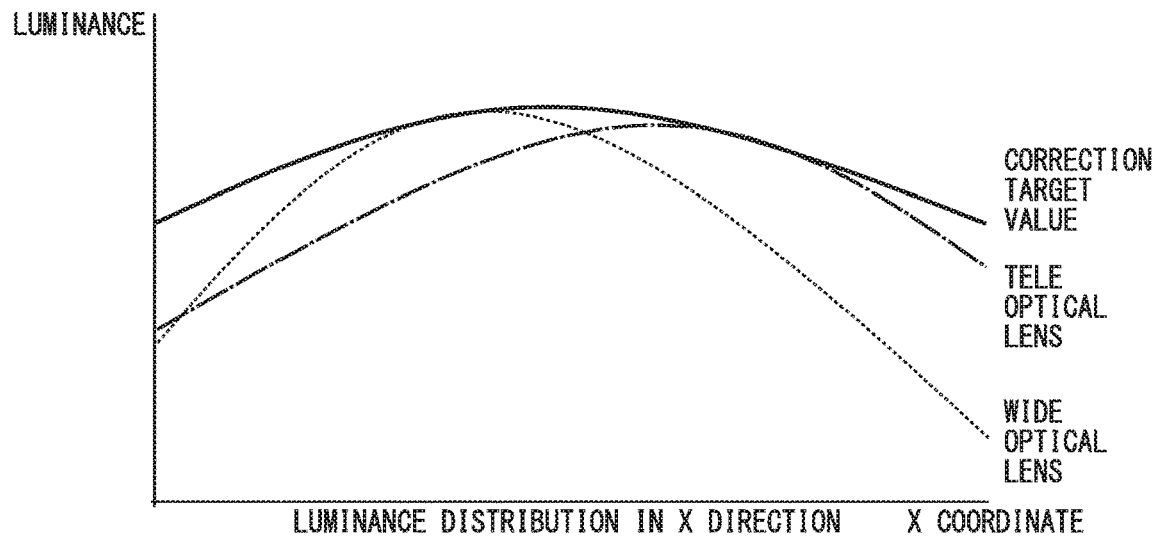

FIG. 5 is a diagram for explaining an example of shading correction processing in the endoscope apparatus 2 (more specifically, the shading correction section 1233*a*) according to the second embodiment of the present invention. FIG. 5 (*a*) shows an example of directions (an X direction (horizontal direction) and a Y direction (vertical direction)) in which different shading appears in the image (video) of the subject to be generated.

First, with reference to FIG. 5 (*b*), the gain value used when the shading correction unit 1233*a* performs the shading correction processing in the Y direction (vertical direction) will be described. FIG. 5 (*b*) shows an example of the relation between the position (Y coordinate) of each pixel corresponding to one row in the center of the image (video) of the subject shown as the Y direction in FIG. 5 (*a*) and the luminance of the image (video) corresponding to each pixel. In the endoscope apparatus 2, when images are captured on the optical paths of the WIDE optical lens 222W and the TELE optical lens 222T, in the image (video) of the subject to be generated, as shown in FIG. 5 (*b*), the center part is the brightest (luminance is high) and the image becomes darker (luminance becomes lower) toward the periphery (left and right in FIG. 5 (*b*)), and thus the vertical shading appears. This vertical shading is due to the arrangement of the respective optical lenses 222 in the optical adapter 22 and the vertical shading characteristics in the respective optical lenses 222. More specifically, in an example of shading in the Y direction (vertical direction) shown in FIG. 5 (*b*), in both of the image (video) of the subject photographed by the optical path of the TELE optical lens 222T and the image (video) of the subject photographed by the optical path of the WIDE optical lens 222W, the central portion is the brightest (luminance is high). This is because the optical lenses 222 are arranged side by side (in the horizontal direction) in the optical adapter 22, the respective optical lenses 222 are the same as those arranged in the same position in the vertical direction, and the incident angles in the vertical direction of the reflected light from the subject entering the optical lens 222 become the same angle. In the example of shading in the Y direction (vertical direction) shown in FIG. 5 (*b*), compared to the image (video) of the subject photographed by the optical path of the TELE optical lens 222T, the image (video) of the subject photographed in the optical path of the WIDE optical lens 222W is darker (lower luminance) toward the periphery. This is due to the difference in vertical shading characteristics between the WIDE optical lens 222W and the TELE optical lens 222T.

In the endoscope apparatus 2, in order to correct the shading appearing in the image (video) of the subject photographed by the optical paths of the WIDE optical lens 222W and the TELE optical lens 222T as shown in FIG. 5 (*b*), a gain value to be used when the shading correction unit 1233*a* performs shading correction processing in the Y direction (vertical direction) is predetermined for each optical lens 222. More specifically, in the endoscope apparatus 2, based on the optical characteristics of the respective optical lenses 222, a value by which the digital value of each pixel is multiplied by the shading correction unit 1233*a* is predetermined as a gain value used for the shading correction processing in the Y direction (vertical direction). That is, in the endoscope apparatus 2, a value to be multiplied by the luminance of each pixel included in the image (video) of the subject captured in the optical path of the WIDE optical lens 222W and the luminance of each pixel included in the image (video) of the subject captured by the optical path of the TELE optical lens 222T is set beforehand as the gain value used for the shading correction processing in the Y direction (vertical direction), in order to make the luminance of each pixel included therein to be the luminance of the correction target value shown in FIG. 5 (*b*). Here, even if the predefined gain value for performing the shading correction processing in the Y direction (vertical direction) is a gain value by which the digital value of the same pixel is multiplied, it is a different value between the WIDE optical lens 222W and the TELE optical lens 222T. Therefore, at the same time as switching to the optical path of the optical lens 222 that emits light to the image sensor 212, the image processing control unit 1231 switches the gain value used when the shading correction unit 1233*a* performs the shading correction processing to the gain value corresponding to the switched optical path of the optical lens 222. As a result, the shading correction unit 1233*a* performs shading correction processing of multiplying the digital value of each pixel by the gain value corresponding to each optical lens 222, using the switched gain value. The shading of the correction target value shown in FIG. 5 (*b*) defines the common brightness (luminance) and shading characteristics that can always be corrected, within a range within which the shading correction unit 1233*a* can perform correction, based on the vertical shading characteristics of the WIDE optical lens 222W and the TELE optical lens 222T which are previously known.

Next, the gain value used when the shading correction unit 1233*a* performs the shading correction processing in the X direction (horizontal direction) will be described with reference to FIG. 5 (*c*). FIG. 5 (*c*) shows an example of the relationship between the position (X coordinate) of each pixel corresponding to one row in the center of the image (video) of the subject shown as the X direction in FIG. 5 (*a*) and the luminance of the image (video) corresponding to each pixel. In the endoscope apparatus 2, when images are captured on the optical paths of the WIDE optical lens 222W and the TELE optical lens 222T, in the image (video) of the subject to be generated, as shown in FIG. 5 (*c*), the center portion is brightest (luminance is high) and becomes darker (lower brightness) toward the periphery (left and right in FIG. 5 (*c*)), and thus shading in the horizontal direction appears. This horizontal shading is due to the arrangement of the respective optical lenses 222 in the optical adapter 22 and the horizontal shading characteristics of the respective optical lenses 222. More specifically, in an example of shading in the X direction (horizontal direction) shown in (c) of FIG. 5, in the image (video) of the subject photographed by the optical path of the TELE optical lens 222T and the image (video) of the subject photographed by the optical path of the WIDE optical lens 222W, the position of the brightest (luminance becomes higher) X coordinates is different. This is because the optical lenses 222 of the optical adapter 22 are arranged side by side (in the horizontal direction), and the respective optical lenses 222 are arranged at the same position in the vertical direction as described above, so the angle of incidence in the horizontal direction of the reflected light from the subject entering each optical lens 222 is different. Also in the example of shading in the X direction (horizontal direction) shown in FIG. 5 (c), as in the example of shading in the Y direction (vertical direction) shown in FIG. 5 (b), the image (video) of the subject captured in the optical path of the WIDE optical lens 222W is more remarkably darker (luminance is lower) than the image (video) of the subject captured in the optical path of the TELE optical lens 222T. This is due to the difference in horizontal shading characteristics between the WIDE optical lens 222W and the TELE optical lens 222T.

In the endoscope apparatus 2, in order to correct the shading appearing in the image (video) of the subject photographed by the optical paths of the WIDE optical lens 222W and the TELE optical lens 222T as shown in FIG. 5 (c), a gain value to be used when the shading correction unit 1233a performs shading correction processing in the X direction (horizontal direction) is predetermined for each optical lens 222. More specifically, in the endoscope apparatus 2, based on the optical characteristics of the respective optical lenses 222, a value by which the shading correction unit 1233a multiplies the digital value of each pixel is predetermined as a gain value used for shading correction processing in the X direction (horizontal direction) so that the shading appearing in the image (video) of the subject after the shading correction becomes the shading of the correction target value shown in FIG. 5 (c). That is, in the endoscope apparatus 2, a value by which to multiply in order for the luminance of each pixel included in the image (video) of the subject captured by the optical path of the WIDE optical lens 222W and the luminance of each pixel included in the image (video) of the subject captured by the optical path of the TELE optical lens 222T to be the luminance of the correction target value shown in FIG. 5 (c) is predetermined as a gain value used for the shading correction processing in the X direction (horizontal direction). Here, regarding the predetermined gain value for performing the shading correction processing in the X direction (horizontal direction), as the predetermined gain value for performing the shading correction processing in the Y direction (vertical direction), even for the gain value to be multiplied by the digital value, the WIDE optical lens 222W and the TELE optical lens 222T have different values. Therefore, at the same time as switching of the gain value used for the shading correction processing in the Y direction (vertical direction), that is, at the same time as switching to the optical path of the optical lens 222 that emits light to the image sensor 212, the image processing control unit 1231 switches the gain value used when the shading correction unit 1233a performs the shading correction processing to the gain value corresponding to the optical path of the switched optical lens 222. As a result, similarly to the shading correction processing in the Y direction (vertical direction), using the switched gain value, the shading correction unit 1233a performs a shading correction process of multiplying the digital value of each pixel by the gain value corresponding to each optical lens 222. Regarding the shading of the correction target value shown in FIG. 5 (c), as well as the shading of the correction target value shown in FIG. 5 (b), a common brightness (luminance) and shading characteristic that can always be corrected are determined within a range in which the shading correction unit 1233a can perform correction, based on the respective vertical shading characteristics of the WIDE optical lens 222W and the TELE optical lens 222T which are previously known.

In the endoscope apparatus 2, such a shading correction process is not performed so that the shading appearing in the image (video) of the subject captured in the optical path of the WIDE optical lens 222W by the shading correction unit 1233a becomes the shading appearing in the image (video) of the subject captured in the optical path of the TELE optical lens 222T. That is, in the endoscope apparatus 2, such a shading correction process is not performed so that the shading correction section 1233a adjusts the shading characteristic of the WIDE optical lens 222W to the shading characteristic of the TELE optical lens 222T. This is because conditions such as the brightness when the endoscope apparatus 2 photographs the subject are various, so even if the shading correction section 1233a performs the shading correction processing, it is not always possible to perform correction so that the shading characteristic of the WIDE optical lens 222W is the same as the shading characteristic of the TELE optical lens 222T. In the endoscope apparatus 2, it is considered that there is little deviation of shading appearing in the image (video) of the subject displayed on the display device 30 when the optical path for emitting light to the image sensor 212 is switched in correcting the shading characteristics of both the optical lenses 222 to the same target characteristic (common characteristic), rather than performing shading correction processing such that the shading characteristic of one optical lens 222 matches the shading characteristic of the other optical lens 222.

Based on the pixel signal (for example, RAW signal) of the subject image whose brightness (luminance) level output from the shading correction unit 1233a has been adjusted, similar to the image generation processing unit 1133 provided in the image processing unit 113 of the endoscope apparatus 1 of the first embodiment, the demosaicking unit 1233b performs the demosaicking processing to convert the pixel signal into an image signal (image data) of a general image format such as YUV 422, for example. As described above, the pixel signal of the subject image whose brightness (luminance) level is adjusted and output from the shading correction unit 1233a is subjected to shading correction processing so as to be a signal (for example, a RAW signal) having the same format as the pixel signal of the subject image output by the image sensor 212, except that the levels of the brightness (luminance) represented by the value (digital value) of each pixel included in the pixel signal are different. Therefore, for example, in the case where the color arrangement of color filters affixed to respective pixels arranged in the imaging region of the image sensor 212 is a Bayer arrangement, as in the image generation processing unit 1133 included in the image processing unit 113 of the endoscope apparatus 1 of the first embodiment, based on information of each pixel included in the pixel signal output from the shading correction unit 1233a, the demosaicking unit 1233b performs demosaicking processing (three-paneling process) for conversion into a luminance signal or a color signal representing the image (video) of the subject. The demosaicking unit 1233b then outputs the demosaicked image signal (image data) to the brightness correction unit 1233c. The processing method of the demosaicking process (three-paneling process) in the demosaicking unit 1233b is the same as the processing method of the existing demosaicking process (three-paneling process), and thus a detailed description thereof will be omitted.

The brightness correction unit 1233c is a digital signal processing unit that performs processing for correcting the overall brightness of the image (video) of the subject that varies depending on the optical characteristics of the WIDE optical lens 222W and the TELE optical lens 222T. In accordance with the control by the image processing control unit 1231, the brightness correction unit 1233c performs brightness correction processing so that the area of the image (video) of the subject in which a subject to be observed or measured is captured has a constant brightness optimum for observation and measurement regardless of the difference in the optical lens 222 and zoom magnification. That is, when the optical path of the optical lens 222 that emits light to the image sensor 212 is switched, and even when the zoom magnification is changed, the brightness correction unit 1233c performs the brightness correction process so that the brightness of the area of at least the central portion in the image (video) of the subject imaged by the optical path of each optical lens 222 is the optimum brightness. More specifically, the brightness correction unit 1233c multiplies a predetermined gain value for each optical lens 222 and zoom magnification so that the brightness of the image (video) of the subject becomes the optimum brightness by the value (digital value) of each pixel included in the image signal (image data) of the subject output by the demosaicking unit 1233b, thereby adjusting the level of the brightness (luminance) represented by the digital value of each pixel.

The image processing control unit 1231 switches the predetermined gain value for each optical lens 222 and zoom magnification by which the brightness correction unit 1233c multiplies each pixel value (digital value). More specifically, when the optical path of the optical lens 222 that emits light to the image sensor 212 is switched in accordance with the zoom magnification instructed by the user of the endoscope apparatus 2 or the electronic zoom magnification is changed, the image processing control unit 1231 switches the gain value used when the brightness correction unit 1233c performs the brightness correction processing. As a result, the brightness correction unit 1233c outputs the image signal of the subject whose brightness (luminance) level has been adjusted with respect to the entire image (video) of the subject using the switched gain value to the image correction unit 1233d as the image signal of the subject output by the demosaicking unit 1233b by demosaicking (three-paneling process). The image signal of the object whose brightness (luminance) level has been adjusted by the brightness correction unit 1233c is also image data of the same format as the image signal of the subject output by the demosaicking unit 1233b by demosaicking (three-paneling process).

Here, an example of the gain value used when the brightness correction unit 1233c performs the brightness correction processing will be described. FIG. 6 is a diagram for explaining an example of brightness correction processing in the endoscope apparatus 2 (more specifically, the brightness correction section 1233c) according to the second embodiment of the present invention. FIG. 6 (a) shows an example of a case where the brightness correction process is performed on the image signal (image data) of the subject captured by the optical path of the WIDE optical lens 222W, and FIG. 6 (b) shows an example of a case where the brightness correction processing is performed on the image signal (image data) of the subject captured by the optical path of the TELE optical lens 222T.

Figure 6A:
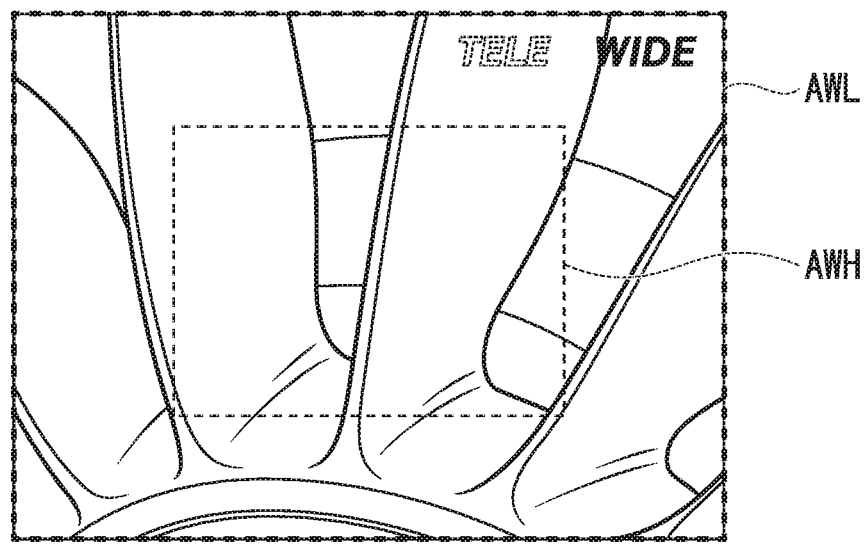
FIGS. 6A and 6B are diagrams for explaining an example of brightness correction processing in an endoscope apparatus according to a second embodiment of the present invention.
Figure 6B:
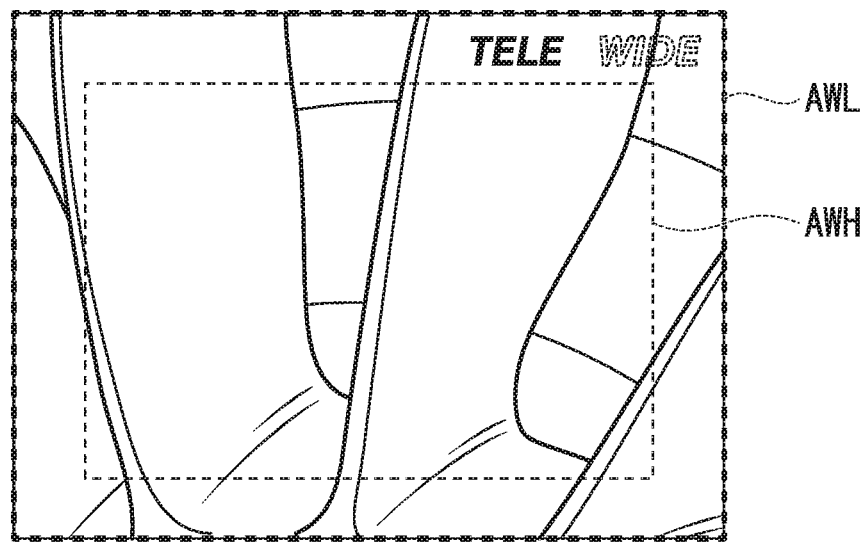

In the endoscope apparatus 2, regions having different weights for adjusting the level of brightness (luminance) are set for each optical lens 222 and zoom magnification. More specifically, the central portion in the image (video) of the captured subject is set as an area for adjusting the level of brightness (luminance) with high weighting, and the other peripheral portions are set as an area for adjusting the level of brightness (luminance) with low weighting. FIG. 6 (a) shows an example in which the central portion of the image (video) of the subject with a certain zoom magnification captured by the optical path of the WIDE optical lens 222W is set as the high weighting area AWH to be multiplied by a high weighted gain value, and the other peripheral portions are set as low weighting areas AWL to be multiplied by a low weighted gain value. FIG. 6 (b) shows an example in which the central portion of the image (video) of the subject of a certain zoom magnification captured by the optical path of the TELE optical lens 222T is set as a high weighting area AWH to be multiplied by a high weighted gain value, and the other peripheral portions are set as low weighting areas AWL to be multiplied by a low weighted gain value. As shown in FIG. 6A and FIG. 6B, the high weighting area AWH set in the image (video) of the subject captured by the optical path of the TELE optical lens 222T is an area larger than the high weighting area AWH set in the image (video) of the subject captured by the optical path of the WIDE optical lens 222W. This is because the angle of view is different between the WIDE optical lens 222W and the TELE optical lens 222T, and the image (video) of the subject captured by the optical path of the TELE optical lens 222T has a larger area in which the subject to be measured is mainly captured.

Then, in the endoscope apparatus 2, gain values corresponding to respective regions used when the brightness correction section 1233c performs the brightness correction processing are predetermined for each optical lens 222 and zoom magnification. That is, in the endoscope apparatus 2, a high weighted gain value, by which image signals (image data) of respective pixels included in the high weighting area AWH set for the image (video) of the subject are multiplied, and a low weighted gain value, by which image signals (image data) of respective pixels included in the low weighting area AWL set for the image (video) of the subject are multiplied, are determined in advance on the basis of the ratio of the optical characteristics in the optical lens 222 (the ratio of brightness and the like) and the zoom magnification. Here, the predetermined gain value for performing the brightness correction process is different for each optical lens 222 and zoom magnification. Therefore, at the same time as switching to the optical path of the optical lens 222 that emits light to the image sensor 212, the image processing control unit 1231 switches each of the gain values used when the brightness correction unit 1233c performs the brightness correction processing to the respective gain values corresponding to the optical path of the switched optical lens 222. Also, at the same time as switching of the electronic zoom magnification in the image (video) of the subject captured by the optical path of each optical lens 222, the image processing control unit 1231 switches each of the gain values used by the brightness correction unit 1233c performing the brightness correction processing to respective gain values corresponding to the electronic zoom magnification in each optical lens 222. As a result, the brightness correction unit 1233c performs brightness correction processing in which the image signal (image data) of each pixel included in each area in the image signal (image data) of the object is multiplied by the weighted gain value corresponding to each switched region, and performs brightness correction processing on the entire image (video) of the subject. Then, the brightness correction unit 1233c outputs to the image correction unit 1233d the pixel signal of the subject in which brightness correction processing was performed so that the brightness of at least the central region in the image (video) of the subject was a constant brightness optimum for observation and measurement.

The high weighting area AWH set in the captured image (video) of the subject corresponds to, for example, a photometric area in an auto exposure (AE) function provided in a general imaging apparatus. However, if the brightness of the entire image (video) of the subject is corrected by a general automatic exposure function, the image of the subject of a plurality of frames is captured and the brightness converges in stages, and a certain amount of time is required until the brightness of the image (video) of the subject becomes constant brightness optimum for observation or measurement. In particular, when the optical path of the optical lens 222 that emits light to the image sensor 212 is switched, since the objective lens is changed to another objective lens having different optical characteristics, much time is required until the brightness of the image (video) of the subject becomes constant brightness. That is, fluctuation in brightness increases in the image (video) of the subject displayed on the display device 30. In this case, the user of the endoscope apparatus 2 confirming the image (video) of the subject displayed on the display device 30 is given an uncomfortable feeling. Therefore, in the endoscope apparatus 2, as described above, the gain values, which correspond to the respective regions and can be uniquely determined based on the combination of the optical characteristic of the optical lens 222 and the zoom magnification that is known in advance, are switched at the same time as switching of the optical lens 222 or changing of the electronic zoom magnification. As a result, the time required for the brightness of the image (image) of the subject to have a certain brightness is shortened. Thus, in the endoscope apparatus 2, fluctuation in brightness in the image (video) of the subject displayed on the display device 30 is reduced.

In the above description, as a processing method of brightness correction in the image (video) of the subject, a method in which image signals (image data) of respective pixels included in respective regions set for each optical lens 222 and zoom magnification are multiplied by a predetermined gain value, thereby correcting the brightness of the image (video) of the subject, has been described. However, as described above, the high weighting area AWH set in the image (video) of the captured subject corresponds to, for example, a photometric area in the automatic exposure function provided in a general imaging apparatus. Therefore, the method of correcting the brightness of the image (video) of the subject is not limited to a method of multiplying the image signal (image data) of each pixel included in each set region by a predetermined gain value. For example, a method in which the image processing control unit 1231 performs the output of the control signal for changing the exposure time when the image sensor 212 picks up the subject image, which is known as shutter speed and is defined in advance for each optical lens 222 and zoom magnification so that an evaluation value (AE evaluation value) of the automatic exposure of the area corresponding to the photometry area becomes constant, to the image sensor 212 together with the switching of the gain value described above may be adopted.

The image correcting unit 1233d is a digital signal processing unit that performs signal processing such as gamma correction processing, contour correction processing, color correction processing, and the like on the image signal (image data) of the subject which is output from the brightness correcting unit 1233c and whose overall brightness (luminance) level is adjusted, similarly to the image generation processing unit 1133 provided in the image processing unit 113 of the endoscope apparatus 1 according to the first embodiment. The gamma correction processing is a process of correcting the nonlinearity between the color of the output image (video) and the color of the image (video) actually displayed on the display device 30 when the image (video) of the subject generated from the image signal (image data) of the subject is displayed on the display device 30. The outline correction process is an edge enhancement process for emphasizing the outline of the subject included in an image (video) of the subject generated from the image signal (image data) of the subject and the position of the edge where the change in luminance and color is large in the image (video). The color correction processing is processing for correcting distortion by an optical system (in particular, the optical lens 222) such as the color shift (magnification chromatic aberration) of the subject included in the image (video) of the subject generated from the image signal (image data) of the subject. As described above, the image signal of the subject which is output from the brightness correction unit 1233c and whose overall brightness (luminance) level is adjusted is a signal (image data) of the same format as the image signal of the subject output by the demosaicking unit 1233b by demosaicking processing (three-paneling process), except that the level of brightness (luminance) represented by the value (digital value) of each pixel included in the image signal is different by the brightness correction processing. Therefore, similarly to the image generation processing unit 1133 provided in the image processing unit 113 of the endoscope apparatus 1 according to the first embodiment, the image correction unit 1233d performs signal processing such as gamma correction processing, contour correction processing, color correction processing, and the like. Then, the image correction unit 1233d outputs the image (video) of the subject generated from the image signal of the subject output by the brightness correction unit 1233c by signal processing to the electronic zoom processing unit 1234. In addition, since the respective processing methods of the gamma correction processing, the contour correction processing, and the color correction processing in the image correction unit 1233d are the same as the respective processing methods of the existing gamma correction processing, contour correction processing, and color correction processing, detailed description will be omitted.

Similarly to the electronic zoom processing unit 1134 provided in the image processing unit 113 of the endoscope apparatus 1 according to the first embodiment, the electronic zoom processing unit 1234 is a digital signal processing unit that generates an enlarged image (video) of the subject by applying electronic zoom processing to the image (video) of the subject output from the image generation processing unit 1233. The electronic zoom processing unit 1234 generates the final image (video) of the subject enlarged to the zoom magnification output from the image processing control unit 1231. The electronic zoom processing unit 1234 outputs the final image (video) of the subject generated by performing the electronic zoom process to the system control unit 111. Since the electronic zoom processing method in the electronic zoom processing unit 1234 is the same as the existing electronic zoom processing method, a detailed description thereof will be omitted.

However, when enlarging the image (video) of the subject output from the image generation processing unit 1233, the electronic zoom processing unit 1234 performs electronic zoom processing with reference to the center position of a predetermined image (video) of the subject so as not to cause a shift in the center position of the image (video) of the subject. More specifically, the electronic zoom processing unit 1234 performs the electronic zoom processing with the center position in the image (video) of the subject captured in the optical path of the TELE optical lens 222T as the center position (hereinafter referred to as a "zoom center") as the reference when performing electronic zoom processing. For example, in the endoscope apparatus 2, similar to the relationship between the position (X coordinate) of each pixel in shading correction in the X direction (horizontal direction) shown in FIG. 5 (*c*) and the luminance of the image (video) corresponding to each pixel, the position of the X coordinate where brightness becomes highest (luminance becomes high) is different between the image (video) of the subject photographed by the optical path of the TELE optical lens 222T and the image (video) of the subject photographed by the optical path of the WIDE optical lens 222W. Here, the position of the X coordinate where brightness becomes highest (luminance becomes high) in the image (video) of the subject is the position of the X coordinate of the center position in the image (video) of the subject photographed by the optical path of each optical lens 222. That is, it represents the position of the optical center in the optical path of each optical lens 222 (hereinafter referred to as "optical center"). In this case, if the electronic zoom processing unit 1234 performs the electronic zoom processing with the center position in the image (video) of the subject photographed by the optical path of each optical lens 222 as the reference (zoom center), when the image processing control unit 1231 switches the optical path of the optical lens 222 that emits light to the image sensor 212, since the center position (optical center) is different, a shift occurs in the center position of the image (video) of the subject displayed on the display device 30. Therefore, in the electronic zoom processing unit 1234, electronic zoom processing is performed on the image (video) of the subject photographed by the optical path of each optical lens 222 with reference to the center position (optical center) of the image (video) of the photographed subject, which can be determined based on the optical characteristics of the TELE optical lens 222T, as a reference (zoom center). That is, the electronic zoom processing unit 1234 sets the center position (zoom center), which is the reference when performing the electronic zoom processing on the image (video) of the subject photographed by the optical path of the WIDE optical lens 222W, to a position corresponding to the center position (optical center) of the image (video) of the subject photographed with the optical path of the TELE optical lens 222T. Thus, in the endoscope apparatus 2, the electronic zoom process can be performed with respect to the same position in the image (video) of the subject photographed by the optical path of either the WIDE optical lens 222W or the TELE optical lens 222T. Thus, in the endoscope apparatus 2, similarly to the endoscope apparatus 1 of the first embodiment, even when enlarging to the same zoom magnification, it is possible to reduce deterioration in image quality of an image (video) of the final photographed subject. Furthermore, even when the optical path of the optical lens 222 that emits light to the image sensor 212 is switched, deviation does not occur in the center position (hereinafter referred to as "display center") of the image (video) of the subject displayed on the display device 30.

With such a configuration, similarly to the endoscope apparatus 1 of the first embodiment, in the endoscope apparatus 2, when the electronic zoom processing unit 1134 performs the electronic zoom processing, the image processing control unit 1231 automatically switches the optical lens 222 provided in the optical adapter 22 according to the zoom magnification instructed by the user of the endoscope apparatus 1. As a result, similarly to the endoscope apparatus 1 of the first embodiment, in the endoscope apparatus 2, in a state where the degradation of the image quality of the enlarged final image (video) of the subject, which is generated by performing the electronic zoom processing by the electronic zoom processing unit 1134 in accordance with the instructed zoom magnification, is reduced (suppressed), it is possible to display it on the display device 30.

Further, in the endoscope apparatus 2, the respective components included in the image generation processing unit 1233 perform processing for absorbing a difference in characteristics between the WIDE optical lens 222W and the TELE optical lens 222T provided in the optical adapter 22. In the endoscope apparatus 2, when the electronic zoom processing unit 1234 provided in the endoscope processing unit 110 generates the final image (video) of the subject to be displayed on the display device 30, electronic zoom processing is performed with the center position (optical center) of the image (video) of the subject captured in the optical path of the TELE optical lens 222T as the reference (zoom center) position. Thus, in the endoscope apparatus 2, even when the optical path of the optical lens 222 that emits light to the image sensor 212 is switched, smooth zooming (enlargement or reduction) is performed without shifting the center position (display center) of the image (video) of the subject displayed on the display device 30.

The control method when zooming is performed in the endoscope apparatus 2 according to the second embodiment is the same as the control method for zooming in the endoscope apparatus 1 of the first embodiment shown in FIG. 2. However, in the endoscope apparatus 2, in addition to the endoscope apparatus 1 according to the first embodiment, a configuration for absorbing a difference in characteristics between the WIDE optical lens 222W and the TELE optical lens 222T provided in the optical adapter 22 is provided. Therefore, in the endoscope apparatus 2, as described above, at the same time when the image processing control unit 1231 switches to the optical path of the optical lens 222 that emits light to the image sensor 212, or simultaneously changes the electronic zoom magnification, the setting for absorbing the difference in characteristics between the WIDE optical lens 222W and the TELE optical lens 222T is switched.

More specifically, at the same time as switching to the optical path of the optical lens 222 that emits light to the image sensor 212, the image processing control unit 1231 switches the gain value used when the shading correction unit 1233a performs the shading correction processing to the gain value corresponding to the optical path of the switched optical lens 222. The process of switching the gain value used when the shading correction unit 1233a in the image processing control unit 1231 performs the shading correction process is a process performed in steps S202 and S301 included in the control method for zooming in the endoscope apparatus 1 of the first embodiment shown in FIG. 2.

At the same time as switching to the optical path of the optical lens 222 that emits light to the image sensor 212, the image processing control unit 1231 switches each gain value, which is used when the brightness correction unit 1233c performs the brightness correction processing, to the respective gain values corresponding to the optical path of the switched optical lens 222. This processing for switching the respective gain values used when the brightness correction unit 1233c in the image processing control unit 1231 performs the brightness correction processing is a process performed in steps S202 and S301 included in the control method for zooming in the endoscope apparatus 1 of the first embodiment shown in FIG. 2.

Also, at the same time as switching of the electronic zoom magnification in the image (video) of the subject captured by the optical path of each optical lens 222, the image processing control unit 1231 switches the respective gain values, which are used when the brightness correction unit 1233c performs the brightness correction processing, to the respective gain values corresponding to the electronic zoom magnification in the respective optical lenses 222. This processing for switching the respective gain values used when the brightness correction unit 1233c in the image processing control unit 1231 performs the brightness correction processing is a process performed in steps S204 and S304 included in the control method for zooming in the endoscope apparatus 1 of the first embodiment shown in FIG. 2.

Further, the electronic zoom processing unit 1234 sets the position of the standard (zoom center) of the electronic zoom as the center position (optical center) of the image (video) of the subject captured by the optical path of the TELE optical lens 222T in the electronic zoom processing. At this time, the electronic zoom processing in the electronic zoom processing unit 1234 is different only in reference position, and is the same as the electronic zoom processing in the electronic zoom processing unit 1134 provided in the image processing unit 113 of the endoscope apparatus 1 of the first embodiment (Steps S204 and S304).

In this manner, in the endoscope apparatus 2, as each component for absorbing the difference in characteristics between the WIDE optical lens 222W and the TELE optical lens 222T provided in the optical adapter 22 is added, processing for switching the corresponding gain value by the image processing control unit 1231 is added. However, each of the switching processes of the image processing control unit 1231 added in the endoscope apparatus 2 is a process performed simultaneously in any corresponding process included in the control method for zooming in the endoscope apparatus 1 of the first embodiment shown in FIG. 2, and only the parameter (gain value) of the process is switched. For this reason, the control method for zooming in the endoscope apparatus 2 of the second embodiment can be thought to be the same as the control method for zooming in the endoscope apparatus 1 of the first embodiment shown in FIG. 2. Therefore, a detailed description of the control method for zooming in the endoscope apparatus 2 will be omitted.

According to the second embodiment, the endoscope apparatus (endoscope apparatus 2) in which the endoscope processing unit (the endoscope processing unit 110) performs the shading correction image processing (shading correction processing by the shading correction unit 1233a) for correcting the shading appearing in the image is configured.

Further, according to the second embodiment, the endoscope apparatus 2 in which the shading correction image processing is performed in such a manner that shading appearing in the image acquired by capturing the first subject image and shading appearing in the image capturing the second subject image become a common correction target value is configured.

Further, according to the second embodiment, the endoscope apparatus 2 in which the endoscope processing unit 110 switches the gain value (the value by which the digital value of each pixel is multiplied) to be the correction target value according to the optical path being switched is configured.

Further, according to the second embodiment, the endoscope apparatus 2 in which the endoscope processing unit 110 performs image processing of brightness correction (processing of brightness correction by the brightness correction unit 1233c) for correcting the brightness of the entire image is configured.

Further, according to the second embodiment, the endoscope apparatus 2 in which the image processing of the brightness correction is performed as, in accordance with the zoom magnification, the first area (high weighting area AWH) in the central portion of the image and the second area (low weighting area AWL) in the periphery portion of the image are set, the brightness is corrected with high weighting of the high weighting area AWH, and the brightness is corrected with low weighting of the low weighting area AWL is configured.

Further, according to the second embodiment, the endoscope apparatus 2 in which the endoscope processing unit 110 switches the weighting gain values corresponding to the high weighting area AWH and the low weighting area AWL (the value by which the digital value of each pixel included in each area is multiplied) according to the switched optical path and the zoom magnification is configured.

As described above, also in the endoscope apparatus 2 according to the second embodiment of the present invention, similarly to the endoscope apparatus 1 of the first embodiment, the distal end portion of the insertion portion 20, that is, the optical adapter 22 mounted on the distal end side of the scope section 21, has a plurality of optical lenses 222 (objective lens) of different optical magnifications (two in the endoscope device 2 of the second embodiment, that is, a wide angle WIDE optical lens 222W and a telephoto TELE optical lens 222T). Also in the endoscope apparatus 2 according to the second embodiment of the present invention, similarly to the endoscope apparatus 1 of the first embodiment, the endoscope processing unit 110 provided in the main body 12 (more specifically, the electronic zoom processing unit 1234) performs electronic zoom processing on the image (video) of the subject that captures the subject image in the object according to the zoom magnification instructed by the user of the endoscope apparatus 2, and generates the final image (video) of the subject to be displayed on the display device 30. At this time, in the endoscope apparatus 2 according to the second embodiment of the present invention, similarly to the endoscope apparatus 1 of the first embodiment, the endoscope processing unit 110 (more specifically, the image processing control unit 1231) determines the zoom magnification instructed by the user of the endoscope apparatus 2 and automatically switches the optical path of one optical lens 222 (objective lens) selected as the optical path for emitting light to the image sensor 212 to the optical path of the other optical lens 222 (objective lens). That is, in the endoscope apparatus 2 according to the second embodiment of the present invention, similarly to the endoscope apparatus 1 of the first embodiment, the electronic zoom magnification with respect to the image (image) of the subject which captured the subject image in the optical path of the WIDE optical lens 222W is limited to the optical magnification of the TELE optical lens 222T. As a result, similarly to the endoscope apparatus 1 of the first embodiment, the endoscope apparatus 2 according to the second embodiment of the present invention can also reduce (suppress) deterioration of the image quality of the image (video) of the subject used for measurement. As a result, similarly to the endoscope apparatus 1 of the first embodiment, the endoscope apparatus 2 according to the second embodiment of the present invention can also improve the inspection accuracy of the subject using the endoscope apparatus 2. Also in the endoscope apparatus 2 according to the second embodiment of the present invention, similarly to the endoscope apparatus 1 of the first embodiment, the zoom magnification instructed by the user of the endoscope apparatus 2 is determined and the optical path of the optical lens 222 (objective lens) is automatically switched, so that the operability of the endoscope apparatus 2 can be improved and complication of inspection using the endoscope apparatus 2 can be reduced. It is possible to suppress deterioration in the inspection accuracy of the subject using the endoscope apparatus 2 due to erroneous operation. Also in the endoscope apparatus 2 according to the second embodiment of the present invention, similarly to the endoscope apparatus 1 of the first embodiment, the zoom magnification instructed by the user of the endoscope apparatus 2 is determined and the image sensor 212 is notified that the light path for emitting light is switched. Thereby, the user of the endoscope apparatus 2 can easily confirm the optical path of the optical lens 222 (objective lens) which is currently selected as the light path for emitting light to the image sensor 212.

Furthermore, in the endoscope apparatus 2 according to the second embodiment of the present invention, components for absorbing a difference in characteristics between the WIDE optical lens 222W and the TELE optical lens 222T provided in the optical adapter 22 are provided. (More specifically, an image processing control unit 1231, a shading correction unit 1233*a* and a brightness correction unit 1233*c* in the image processing unit 123.) Thus, in the endoscope apparatus 2 according to the second embodiment of the present invention, even when the optical path of the optical lens 222 (objective lens) that emits light to the image sensor 212 is switched, it is possible to suppress a deviation in the brightness of the final image (image) of the subject to be displayed on the display device 30 due to the difference in the characteristics of the optical lens 222. Thus, in the endoscope apparatus 2 according to the second embodiment of the present invention, it is possible to reduce (suppress) the deterioration of the image quality of the final image (video) of the subject to be displayed on the display device 30. Further, in the endoscope apparatus 2 according to the second embodiment of the present invention, when generating the final image (video) of the subject to be displayed on the display device 30, the endoscope processing unit 110 (more specifically, the electronic zoom processing unit 1234) provided in the main body 12 performs electronic zooming processing with the center position (optical center) of the image (video) of the subject captured by the optical path of the TELE optical lens 222T as the reference (zoom center) position. Thus, in the endoscope apparatus 2 according to the second embodiment of the present invention, even when the optical path of the optical lens 222 (objective lens) that emits light to the image sensor 212 is switched, it is possible to smoothly zoom (enlarge or reduce) without shifting the center position (display center) of the image (video) of the subject displayed on the display device 30.

As described above, according to the embodiments for performing the present invention, in an endoscope apparatus equipped with an optical adapter equipped with two objective lenses having different optical magnifications and configured to switch an optical path for causing light of a subject image to be incident on an imaging element and provided on a distal end side of a scope section constituting an insertion section, an endoscope processing unit that switches an optical path through which light enters the imaging device according to a zoom magnification instructed by a user of the endoscope apparatus 1 is provided. In an embodiment for performing the present invention, when enlarging an image (video) for measurement or observation of the subject captured by the optical system of the objective lens having a lower optical magnification by the electronic zoom process, the endoscope processing unit limits the zoom magnification to the optical magnification of the objective lens having the higher optical magnification. When a zoom magnification higher than that is instructed, the optical system for imaging the subject is automatically switched to the optical system of the objective lens having the higher optical magnification. Further, in an embodiment for performing the present invention, the endoscope processing unit notifies that the optical system of the objective lens has been switched. Thereby, in the embodiment for performing the present invention, it is possible to suppress the zoom magnification of the electronic zoom process applied to the image (video) for measuring and observing the subject to a low level, so that it is possible to reduce (suppress) deterioration of image quality of an image (video) for measuring and observing the subject. Furthermore, in the embodiment for performing the present invention, there is no need for the user of the endoscope apparatus to perform an operation for switching the optical path for inputting light to the imaging element, and it is possible to improve the operability of the endoscope apparatus and to alleviate the complication of the inspection using the endoscope apparatus. Further, in the embodiment for performing the present invention, it is possible for the user of the endoscope apparatus to easily confirm that the optical path for allowing light to enter the imaging element is switched.

Further, according to an embodiment for performing the present invention, an image processing unit is provided in the endoscope processing unit for absorbing a difference in optical characteristics between two objective lenses having different optical magnifications provided in the optical adapter. Thus, in the embodiment for performing the present invention, even when an optical system for imaging the subject is switched, it is possible to reduce (suppress) the deterioration of the image quality of the image (video) for measuring and observing the subject due to the difference in the optical characteristics of the objective lens. Further, in the embodiment for performing the present invention, when measuring or observing the subject by using any optical system, the standard for applying the electronic zoom process to the image (video) of the subject is set as the center position (optical center) of the objective lens having the higher optical magnification. Thereby, in the embodiment for performing the present invention, even when the optical system for imaging the subject is switched, no deviation occurs in the center position (zoom center) of the image (video) that has been subjected to the electronic zoom process, and the difference in the image quality of the image (image) for measuring and observing the subject can be reduced.

As a result, according to the embodiment performing the present invention, it is possible to improve the inspection accuracy when measuring and observing the subject.

In each embodiment, the configuration of the endoscope apparatus having the insertion portion configured by the scope and the optical adapter is described. In other words, according to the embodiments, the endoscope apparatus having the configuration such that the objective optical system configuring the insertion portion can be separated from the distal end side of the insertion portion is described. However, the configuration of the insertion portion configuring the endoscope apparatus is not limited to the configuration described in each embodiment, and the scope and the optical adapter may be integrated. In other words, the insertion portion of the endoscope apparatus may be configured such that the objective optical system is incorporated in the distal end side of the insertion portion.

In the embodiments, it is described that the length of the scope configuring the insertion portion is extremely long. However, the point of view of each embodiment is that the endoscope apparatus is not limited to the configuration having the insertion portion with an extremely long scope, and the configuration can be applied regardless of the length of the scope configuring the insertion portion. In this case, the same effect can be achieved. In the endoscope apparatus configured to have an insertion portion with a short scope, removing the configuration elements suitable for the endoscope apparatus having the insertion portion with a long scope (more specifically, the light source drive circuit 130, the control signal drive circuit 140, the limiting amplifier circuit 150, and the optical path switching drive circuit 160) can be considered. In this case, the operations, the processing, and the control methods of the endoscope apparatus can be easily considered according to the description in each of the embodiments. Accordingly, detailed description of the endoscope apparatus configured to have the insertion portion with a short scope based on the principle approach of the present invention will be omitted.

According to the embodiments, the endoscope apparatus of the present invention is described as an industrial endoscope apparatus. However, the configuration and the point of view of each embodiment is not limited to the industrial endoscope apparatus. For example, the configuration according to each embodiment can be applied in a medical endoscope apparatus. Accordingly, in the medical endoscope apparatus, the same effect as with the industrial endoscope apparatus described in each embodiment of the present invention can be achieved.

For example, the functions and the processing of the endoscope apparatus such as the main body 10 and a part of the main body 10, the endoscope processing unit 110 provided in the main body 10, the image processing unit 113 provided in the endoscope processing unit 110, and the image processing control unit 1131 provided in the image processing unit 113 may be performed by recording the program for realizing the functions and the processing of the endoscope apparatus in a computer-readable recording medium and causing a computer system to read and execute the program recorded in the recording medium. Here, the computer system is a system including an operating system (OS) and hardware such as peripheral devices. In the case of using the WWW (World Wide Web), "computer system" also includes the homepage providing environment (or displaying environment). "Computer-readable recording medium" refers to a writable non-transitory memory such as a flexible disk, a magneto-optical disc, a read-only memory, and a flash memory, a removable medium such as CD-ROM, and a storage device such as a hard disk drive disposed inside the computer system.

Furthermore, "computer-readable recording medium" also includes a volatile memory (for example, Dynamic Random Access Memory, DRAM) for maintaining the program for a certain period disposed inside the computer system as the server and the client in a case that the program is transferred through a network such as the Internet or a communication line such as a telephone line. The program may be transferred from the computer system storing the program in the memory device to another computer system via a transmission medium or transmission waves in the transmission medium. The "transmission medium" for transmitting the program is a medium having the information transmission function, for example, a network such as the Internet (communication network) or a communication line such as a telephone line. The program may be a program for realizing part of the functions described above. Furthermore, the functions described above may be combined with the program already recorded in the computer system to be realized, that is, the functions may be a difference file (difference program).

As described above, the feature of the present invention is the cooperation control between the TELE/WIDE switching and the electronic ZOOM. The user seamlessly switches between TELE/WIDE by one touch operation. When executing the TELE/WIDE switching, the electronic ZOOM is controlled so as to reach the image center and the field angle. The light distribution of the light source changes by TELE/WIDE switching. Taking this into consideration, the shading correction amount is switched. Screen brightness changes by TELE/WIDE switching. Taking this into consideration, AGC gain and shutter speed are switched. Automatically switched to the TELE state at the timing when the magnification (field angle) of the electronic ZOOM reaches the same magnification as the TELE state. In order to present to the user that TELE/WIDE has been switched, the status of TELE/WIDE is displayed on the screen. When the user keeps pushing the ZOOM button and enters the TELE state, the ZOOM operation is temporarily stopped, the status display of TELE/WIDE is changed, and ZOOM continues again.

Although preferred embodiments of the present invention have been described above, the present invention is not limited to these embodiments and modifications thereof. Additions, omissions, substitutions, and other changes in the configuration are possible without departing from the spirit of the present invention. Also, the present invention is not limited by the foregoing description, but is limited only by the scope of the appended claims.

What is claimed is:

1. An endoscope apparatus comprising:
   an insertion portion;
   an actuator configured to switch between a first optical path and a second optical path so that only one of a first subject image and a second subject image is imaged on an image forming area where the first subject image and the second subject image are commonly focused, the first subject image being an image of a subject formed by light emitted from a first objective optical system disposed at a distal end of the insertion portion, the second subject image being an image of the subject formed by light emitted from a second objective optical system disposed at the distal end of the insertion portion and having an optical magnification higher than that of the first objective optical system; and a processor configured to:

receive instruction for zoom magnification;

perform a comparison of the zoom magnification instructed with the optical magnification of the second objective optical system;

control the actuator to switch to one of the first optical path so that the first subject image is formed on the image forming area and the second optical path so that the second subject image is formed on the image forming area, based on a result of the comparison of the zoom magnification with the optical magnification of the second objective optical system;

control an image sensor to acquire one of a first image based on the first subject image formed by the first optical path and a second image based on the second subject image formed by the second optical path; and apply image processing to the one of the first image and the second image acquired by the image sensor.

2. The endoscope apparatus according to claim 1, wherein the processor is configured to:

control the actuator to switch to the second optical path based on a result of the comparison being that the zoom magnification instructed is equal to or greater than the optical magnification of the second objective optical system; and control the actuator to switch to the first optical path based on a result of the comparison being that the zoom magnification instructed is lower than the optical magnification of the second objective optical system.

3. The endoscope apparatus according to claim 2, wherein the processor is configured to change parameters of the image processing based on the one of the first optical path and the second optical path being switched.

4. The endoscope apparatus according to claim 1, wherein, in applying the image processing, the processor is configured to perform image processing of electronic zoom for enlarging the one of the first image and the second image acquired by the image sensor.

5. The endoscope apparatus according to claim 4, wherein, in performing the image processing of the electronic zoom, the processor is configured to enlarge the one of the first image and the second image acquired by the image sensor based on the zoom magnification instructed.

6. The endoscope apparatus according to claim 5, wherein, in performing the image processing of the electronic zoom, the processor is configured to change the electronic zoom magnification based on the zoom magnification instructed and the one of the first optical path and the second optical path being switched.

7. The endoscope apparatus according to claim 6, wherein the processor is configured to:

set a magnification acquired by dividing the zoom magnification instructed by the optical magnification of the second objective optical system as the electronic zoom magnification based on a switch to the second optical path; and set the zoom magnification instructed as the electronic zoom magnification based on a switch to the first optical path.

8. The endoscope apparatus according to claim 4, wherein the processor is configured to set a center position of the second image as a center position of an enlarged image generated by the image processing of the electronic zoom.

9. The endoscope apparatus according to claim 4, wherein the processor is configured to perform image processing of shading correction for correcting shading appearing in the one of the first image and the second image acquired by the image sensor.

10. The endoscope apparatus according to claim 9, wherein, in the image processing of the shading correction, the processor is configured to correct each of shading appearing in the first image and shading appearing in the second image to be a common correction target value.

11. The endoscope apparatus according to claim 10, wherein the processor is configured to switch a gain value for setting the common correction target value based on the one of the first optical path and the second optical path being switched.

12. The endoscope apparatus according to claim 4, wherein the processor is configured to perform image processing of brightness correction for correcting an overall brightness of the one of the first image and the second image acquired by the image sensor.

13. The endoscope apparatus according to claim 12, wherein, in the image processing for the brightness correction, the processor is configured to:

set a first area at a center portion of the one of the first image and the second image and a second area at a peripheral portion of the one of the first image and the second image, based on the zoom magnification; and correct a brightness of the first area with high weighting and a brightness of the second area with low weighting.

14. The endoscope apparatus according to claim 13, wherein the processor is configured to switch each weighting gain value corresponding to the first area and the second area based on the one of the first optical path and the second optical path being switched and the zoom magnification.

15. The endoscope apparatus according to claim 1, wherein the processor is configured to output an optical path switching drive signal to the actuator when switching between the first optical path and the second optical path, and wherein the actuator is configured to move a light shield that shields one of the first optical path and the second optical path by a magnetic field generated based on a polarity of a current in the optical path switching drive signal to shield the other of the first optical path and the second optical path.

16. The endoscope apparatus according to claim 1, wherein the insertion portion comprises:

an elongated cord portion; and an optical adapter detachably attached to a distal end side of the elongated scope portion, wherein the first objective optical system, the second objective optical system, and the actuator are disposed within the optical adapter, and wherein the image sensor is disposed on the distal end side of the elongated scope portion.

17. The endoscope apparatus according to claim 1,
wherein the processor is configured to control a display to provide notification of a switch to the first optical path and notification of a switch to the second optical path.

18. A control method of an endoscope apparatus, wherein the endoscope apparatus includes:
an insertion portion; and
an actuator configured to switch between a first optical path and a second optical path so that only one of a first subject image and a second subject image is imaged on an image forming area where the first subject image and the second subject image are commonly focused, the first subject image being an image of a subject formed by light emitted from a first objective optical system disposed at a distal end of the insertion portion, the second subject image being an image of the subject formed by light emitted from a second objective optical system disposed at the distal end of the insertion portion and having an optical magnification higher than that of the first objective optical system,
wherein the control method comprises:
receiving instruction for zoom magnification;
performing a comparison of the zoom magnification instructed with the optical magnification of the second objective optical system;
controlling the actuator to switch to one of the first optical path so that the first subject image is formed on the image forming area and the second optical path so that the second subject image is formed on the image forming area, based on a result of the comparison of the zoom magnification with the optical magnification of the second objective optical system;
controlling an image sensor to acquire one of a first image based on the first subject image formed by the first optical path and a second image based on the second subject image formed by the second optical path; and
applying image processing to the one of the first image and the second image acquired by the image sensor.

19. A non-transitory computer-readable recording medium storing a program for controlling an endoscope apparatus, wherein the endoscope apparatus includes:
an insertion portion; and
an actuator configured to switch between a first optical path and a second optical path so that only one of a first subject image and a second subject image is imaged on an image forming area where the first subject image and the second subject image are commonly focused, the first subject image being an image of a subject formed by light emitted from a first objective optical system disposed at a distal end of the insertion portion, the second subject image being an image of the subject formed by light emitted from a second objective optical system disposed at the distal end of the insertion portion and having an optical magnification higher than that of the first objective optical system,
wherein the program causes a computer to execute:
receiving instruction for zoom magnification;
performing a comparison of the zoom magnification instructed with the optical magnification of the second objective optical system;
controlling the actuator to switch to one of the first optical path so that the first subject image is formed on the image forming area and the second optical path so that the second subject image is formed on the image forming area, based on a result of the comparison of the zoom magnification with the optical magnification of the second objective optical system;
controlling an image sensor to acquire one of a first image based on the first subject image formed by the first optical path and a second image based on the second subject image formed by the second optical path; and
applying image processing to the one of the first image and the second image acquired by the image sensor.

* * * * *